(12) United States Patent
Moriguchi et al.

(10) Patent No.: US 9,486,134 B2
(45) Date of Patent: Nov. 8, 2016

(54) OPHTHALMOLOGIC IMAGING APPARATUS AND OPHTHALMOLOGIC IMAGE PROCESSING APPARATUS

(71) Applicant: KABUSHIKI KAISHA TOPCON, Itabashi-ku (JP)

(72) Inventors: Yoshikiyo Moriguchi, Itabashi-ku (JP); Masahiro Akiba, Toda (JP)

(73) Assignee: KABUSHIKI KAISHA TOPCON, Itabashi-ku (JP)

( * ) Notice: Subject to any disclaimer, the term of this patent is extended or adjusted under 35 U.S.C. 154(b) by 187 days.

(21) Appl. No.: 14/401,751

(22) PCT Filed: Apr. 30, 2013

(86) PCT No.: PCT/JP2013/062597
§ 371 (c)(1),
(2) Date: Nov. 17, 2014

(87) PCT Pub. No.: WO2013/187146
PCT Pub. Date: Dec. 19, 2013

(65) Prior Publication Data
US 2015/0138502 A1 May 21, 2015

(30) Foreign Application Priority Data

Jun. 11, 2012 (JP) .................................. 2012-131534

(51) Int. Cl.
*A61B 3/14* (2006.01)
*A61B 3/00* (2006.01)
*A61B 3/10* (2006.01)

(52) U.S. Cl.
CPC ............ *A61B 3/0025* (2013.01); *A61B 3/0058* (2013.01); *A61B 3/10* (2013.01); *A61B 3/102* (2013.01); *A61B 3/14* (2013.01)

(58) Field of Classification Search
CPC .. A61B 3/0041; A61B 3/005; A61B 3/0058; A61B 3/102; A61B 3/1025; A61B 3/113; A61B 3/14; A61B 3/15; A61B 3/152
USPC ................. 351/205, 206, 221, 246
See application file for complete search history.

(56) References Cited

U.S. PATENT DOCUMENTS

| 6,377,349 B1 | 4/2002 | Fercher |
| 7,345,770 B2 | 3/2008 | Chan et al. |
| 2010/0110172 A1 | 5/2010 | Satake |

FOREIGN PATENT DOCUMENTS

| EP | 2 184 006 A1 | 5/2010 |
| JP | 9 276232 | 10/1997 |

(Continued)

OTHER PUBLICATIONS

Extended European Search Report issued Feb. 1, 2016 in Patent Application No. 13805162.8.

(Continued)

*Primary Examiner* — Huy K Mai
(74) *Attorney, Agent, or Firm* — Oblon, McClelland, Maier & Neustadt, L.L.P.

(57) ABSTRACT

An ophthalmologic imaging apparatus that can follow up imaging for acquiring a cross sectional image by referring to a front image of an eye acquired in the past and scanning the same position as before with light, includes: a photographing part configured to photograph the eye and acquire a front image thereof; a cross sectional image forming part configured to scan the eye with light and form a cross sectional image thereof; a storage configured to store a first front image of the eye and a second front image acquired in follow up imaging executed with referring to the first front image; an information obtaining part configured to analyze the first and second front images and obtain misregistration information between these front images; and a calculator configured to calculate an evaluation value of an error in a scanning position in the follow up imaging based on the misregistration information.

25 Claims, 12 Drawing Sheets

(56) References Cited

FOREIGN PATENT DOCUMENTS

| JP | 11 325849 | 11/1999 | | |
|---|---|---|---|---|
| JP | 2002 139421 | 5/2002 | | |
| JP | 2006 153838 | 6/2006 | | |
| JP | 2007 24677 | 2/2007 | | |
| JP | 2008 61848 | 3/2008 | | |
| JP | 2008 73099 | 4/2008 | | |
| JP | 2008 259544 | 10/2008 | | |
| JP | 2009 11381 | 1/2009 | | |
| JP | 2010 110391 | 5/2010 | | |
| JP | 2011 50430 | 3/2011 | | |
| JP | 2011 115507 | 6/2011 | | |
| JP | 2011 212213 | 10/2011 | | |
| JP | 2011-212213 | * 10/2011 | ............... | A61B 3/12 |
| JP | 2012 16620 | 1/2012 | | |

OTHER PUBLICATIONS

International Search Report Issued Jul. 23, 2013 in PCT/JP13/062597 Filed Apr. 30, 2013.

* cited by examiner

OPHTHALMOLOGIC IMAGING APPARATUS AND OPHTHALMOLOGIC IMAGE PROCESSING APPARATUS

TECHNICAL FIELD

The present invention relates to an ophthalmologic imaging apparatus and an ophthalmologic image processing apparatus.

BACKGROUND TECHNOLOGY

In recent years, optical coherence tomography (OCT) has attracted attention as an apparatus for imaging an eye using optical scanning. Unlike an X-ray CT apparatus, optical coherence tomography is noninvasive to human bodies, and is therefore expected to be utilized in the medical field and biological field. For example, in the ophthalmology, apparatuses that form images of a fundus and cornea or the like are in a practical stage.

The apparatus disclosed in Patent Document 1 uses a technique of so-called "Fourier Domain OCT." That is to say, the apparatus irradiates a low-coherence light beam to an object, superposes the reflected light and the reference light to generate an interference light, and acquires the spectral intensity distribution of the interference light to execute Fourier transform, thereby imaging the morphology in the depth direction (the z-direction) of the object. Furthermore, the apparatus is provided with a galvano mirror that scans a light beam (signal light) along one direction (x-direction) perpendicular to the z-direction, and is thereby configured to form an image of a desired measurement target region of the object. An image formed by this apparatus is a two-dimensional cross sectional image in the depth direction (z-direction) along the scanning direction (x-direction) of the light beam. The technique of this type is also called Spectral Domain.

Patent Document 2 discloses a technique of scanning with a signal light in the horizontal direction (x-direction) and the vertical direction (y-direction) to form multiple two-dimensional cross sectional images in the horizontal direction, and acquiring and imaging three-dimensional cross sectional information of a measured range based on the cross sectional images. As the three-dimensional imaging, for example, a method of arranging and displaying multiple cross sectional images in the vertical direction (referred to as stack data or the like), or a method of executing a rendering process on volume data (voxel data) based on stack data to form a three-dimensional image may be considered.

Patent Documents 3 and 4 disclose other types of OCT apparatuses. Patent Document 3 describes an OCT apparatus that images the morphology of an object by sweeping the wavelength of light that is irradiated to an object (wavelength sweeping), detecting interference light obtained by superposing the reflected lights of the light of the respective wavelengths on the reference light to acquire its spectral intensity distribution, and executing Fourier transform. Such an OCT apparatus is called a Swept Source type or the like. The Swept Source type is a kind of the Fourier Domain type.

Further, Patent Document 4 describes an OCT device that irradiates a light having a predetermined beam diameter to an object and analyzes the components of an interference light obtained by superposing the reflected light and the reference light, thereby forming an image of the object in a cross-section orthogonal to the travelling direction of the light. Such an OCT device is called a full-field type, en-face type or the like.

Patent Document 5 discloses an example of applying OCT to the ophthalmologic field. It should be noted that, before OCT was applied, a retinal camera, a slit lamp microscope, a scanning laser opthalmoscope (SLO) etc. were used as apparatuses for observing an eye (see Patent Documents 6, 7 and 8 for example). The retinal camera is an apparatus that photographs the fundus by projecting illumination light onto the eye and receiving the reflected light from the fundus. The slit lamp microscope is an apparatus that obtains an image of the cross-section of the cornea by cutting off the light section of the cornea using slit light. The SLO is an apparatus that images morphology of retinal surface by scanning a fundus by laser light and detecting reflected light thereof with a highly sensitive imaging element such as a photomultiplier.

The apparatus with OCT is superior relative to the retinal camera, etc. in that high-definition images can be obtained, further in that cross sectional images and three-dimensional images can be obtained, etc.

Thus, the apparatus using OCT can be used for observation of various regions of the eye and is capable of obtaining high-definition images, and therefore, has been applied to the diagnosis of various ophthalmologic disorders.

Now, in various medical fields, examinations of same sites of a subject are repeated (sometimes referred to as follow up). Examples of follow up include progress observations and preoperative/postoperative observations. There are specific problems in ophthalmology regarding follow up. Specifically, it is difficult to examine a same site repeatedly because of influences of eye movement (involuntary eye movement during fixation, rotation, etc.) of a subject eye. In particular, reproducing the same scanning position as a past examination is extremely difficult for an imaging apparatus of the type that scans an eye with light.

Patent Documents 9 to 11 discloses technologies that can be applied for solving such a problem of follow up imaging.

The purpose of an invention disclosed in Patent Document 9 is to smoothly detect misregistration (including rotational transfer) between fundus images. For this purpose, this invention is configured to detect an amount of misregistration between fundus images by collating a plurality of subregion images cut from the respective fundus images.

The purpose of an invention disclosed in Patent Document 10 is to preferably detect retinal endogenous signals of a human eye by continuously measuring the same cross sectional site of a fundus. For this purpose, this invention is configured to detect displacements of scanning positions by irradiating and detecting a second light beam while scanning the fundus with a measuring light beam and control a second optical scanner based on the detection results, thereby correcting the scanning positions of the measuring light beam as required. Further, it is also described that template matching based on characteristic regions in retinal front images is utilized for detecting misregistration of scanning positions.

The purpose of an invention disclosed in Patent Document 11 is to correctly irradiate a light beam to a preset position on a fundus regardless of eye movement. For this purpose, this invention is configured to detect picture angle information of scanning light and misregistration information of the fundus based on fundus front images and correct scanning positions of scanning light based on these information.

PRIOR ART DOCUMENTS

Patent Documents

[Patent Document 1]
Japanese Unexamined Patent Application Publication No. H11-325849
[Patent Document 2]
Japanese Unexamined Patent Application Publication No. 2002-139421
[Patent Document 3]
Japanese Unexamined Patent Application Publication No. 2007-24677
[Patent Document 4]
Japanese Unexamined Patent Application Publication No. 2006-153838
[Patent Document 5]
Japanese Unexamined Patent Application Publication No. 2008-73099
[Patent Document 6]
Japanese Unexamined Patent Application Publication No. H09-276232
[Patent Document 7]
Japanese Unexamined Patent Application Publication No. 2008-259544
[Patent Document 8]
Japanese Unexamined Patent Application Publication No. 2009-11381
[Patent Document 9]
Japanese Unexamined Patent Application Publication No. 2011-50430
[Patent Document 10]
Japanese Unexamined Patent Application Publication No. 2011-115507
[Patent Document 11]
Japanese Unexamined Patent Application Publication No. 2011-212213

SUMMARY OF THE INVENTION

Problem that the Invention is to Solve

In follow up imaging, it is very important to realize a degree of an error (accuracy, precision), that is, a degree of misregistration of scanning positions between imagings carried out different timings. Therefore, in order to carry out diagnosis precisely, it is very important to know whether or not follow up imaging has carried out properly, and further, degrees of accuracy and precision of the follow up imaging. However, according to conventional technologies, it has been impossible to quantitatively evaluate degrees of errors in follow up imaging.

For example, the technology disclosed in Patent Document 9 may detect the amount of misregistration between fundus images; however, it is impossible to provide, for users, meanings of misregistration and information indicating whether or not the follow up imaging is appropriate. Thus, the user has to judge by himself based on the misregistration detected. However, it is difficult to judge whether or not the follow up imaging is appropriate since errors of scanning start position in follow up imaging is usually of millimeter order or smaller. Further, there are various types of misregistration such as parallel shifts and rotational shifts, and it has been impossible to evaluate misregistration at least from the perspective of appropriateness/inappropriateness of follow up imaging.

Further, technologies disclosed in Patent Documents 10 and 11 detect misregistration during imaging and correct scanning positions. However, even though such correction is carried out, there still remains misregistration of scanning positions, that is, errors in follow up imaging. These conventional technologies cannot quantitatively evaluate such errors in follow up imaging.

The present invention is developed in order to solve such problems, and its purpose is to provide a technology that is capable of quantitatively evaluating degrees of errors in follow up imaging.

Means for Solving the Problem

An aspects the present invention is an ophthalmologic imaging apparatus capable of carrying out follow up imaging for acquiring a cross sectional image by referring to a front image of an eye acquired in the past and scanning the same position as before with light, comprising: a photographing part configured to photograph the eye and acquire a front image thereof; a cross sectional image forming part configured to scan the eye with light and form a cross sectional image thereof; a storage configured to store a first front image of the eye and a second front image acquired in follow up imaging carried out with referring to the first front image; an information obtaining part configured to analyze the first and second front images and obtain misregistration information between these front images; and a calculator configured to calculate an evaluation value of an error in a scanning position in the follow up imaging based on the misregistration information.

Effect of the Invention

According to the present invention, it is possible to quantitatively evaluate degrees of errors in follow up imaging.

MODE FOR CARRYING OUT THE INVENTION

Examples of embodiments of an ophthalmological imaging apparatus and ophthalmological image processing apparatus according to the present invention will be described in detail with reference to the drawings. The ophthalmologic imaging apparatus according to the present invention forms a cross sectional image and three-dimensional image of an eye fundus by using OCT. In this description, images obtained by OCT are sometimes referred to as OCT images. Further, a measurement operation for forming an OCT image is sometimes referred to as OCT measurement. It should be noted that the contents described in the documents cited in this description may be applied to the following embodiments.

In the following embodiments, configurations in which Fourier Domain OCT is employed will be described in detail. Particularly, ophthalmologic imaging apparatuses according to the following embodiments are capable of obtaining both a fundus OCT image with Spectral Domain OCT and a fundus image, which is similar to the apparatus disclosed in Patent Document 5. It should be noted that configurations according to the present invention may be applied to an ophthalmologic imaging apparatus of any type other than Spectral Domain (for example, Swept Source OCT).

Further, although the following embodiments include a retinal camera as a configuration for acquiring front images of an eye, other imaging apparatus may be applied such as an SLO, slit lamp microscope, ophthalmologic operation microscope, etc. It should be noted that front images of an eye are images acquired by photographing a desired site of the eye (fundus, anterior eye part, etc.) from a viewpoint confronting the eye.

Further, an ophthalmological image processing apparatus according to the present invention may be configured as a part of an ophthalmological imaging apparatus, may be configured as a single computer, or may be configured as two or more computers connected via a network.

First Embodiment

Configurations

Figure 1:
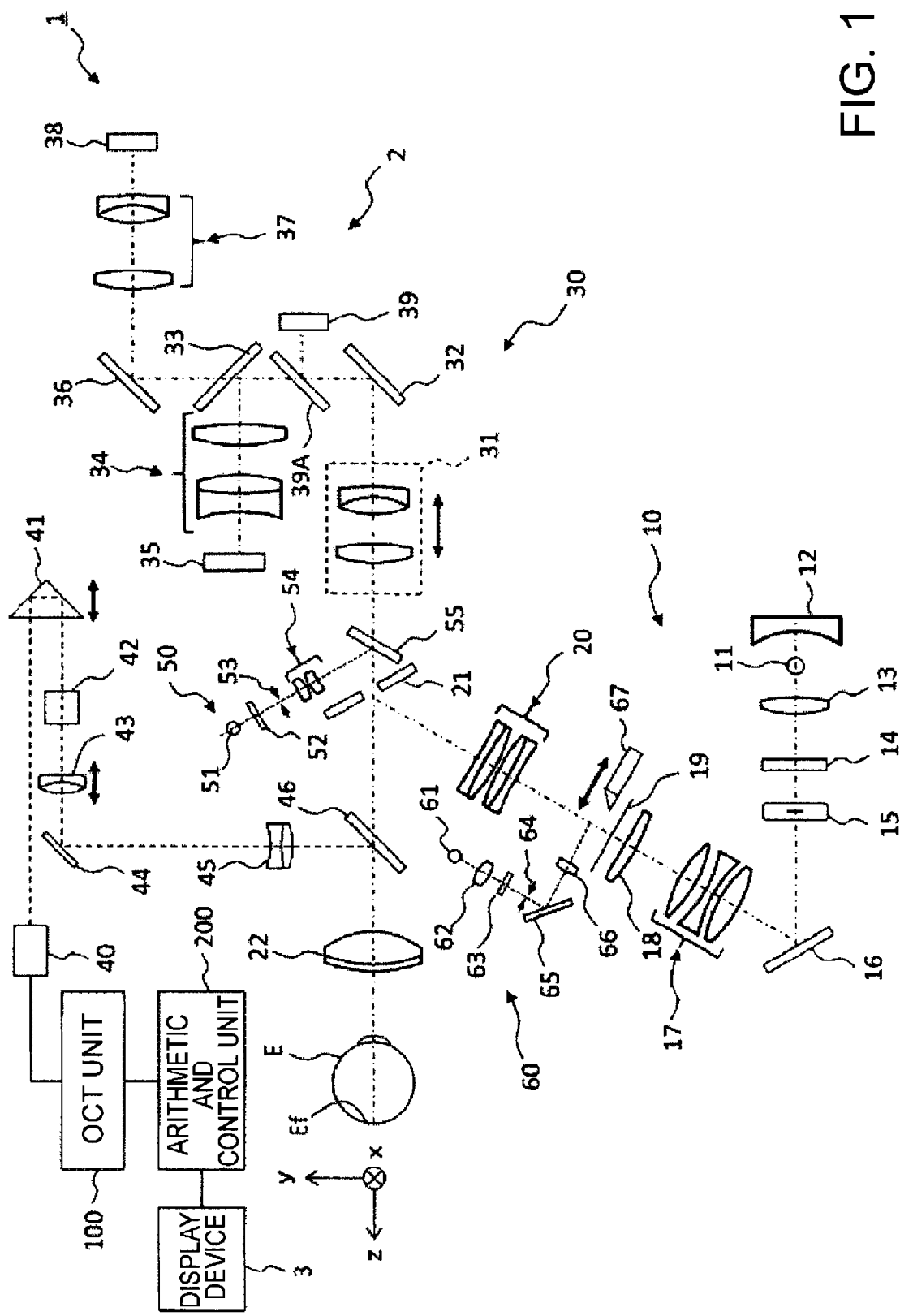
FIG. 1 is a schematic diagram showing an example of a configuration of an ophthalmologic imaging apparatus according to an embodiment.
Figure 2:
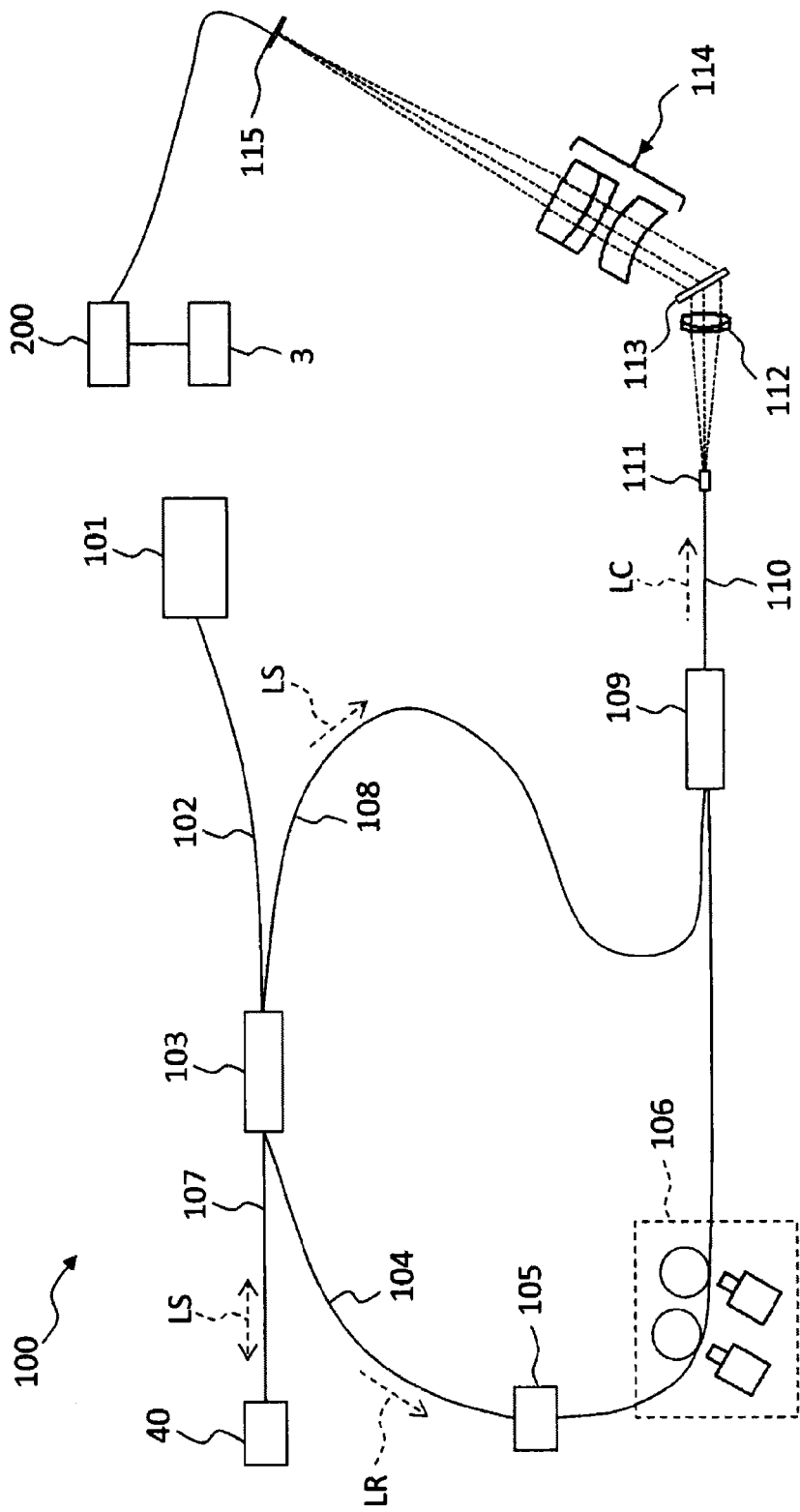
FIG. 2 is a schematic diagram showing an example of a configuration of an ophthalmologic imaging apparatus according to an embodiment.

An ophthalmologic imaging apparatus 1, as shown in FIG. 1 and FIG. 2, includes a retinal camera unit 2, an OCT unit 100, and an arithmetic and control unit 200. The retinal camera unit 2 has almost the same optical system as a conventional retinal camera. The OCT unit 100 is provided with an optical system for obtaining an OCT image of a fundus. The arithmetic and control unit 200 is provided with a computer that executes various arithmetic processes, control processes, and so on.

[Retinal Camera Unit]

The retinal camera unit 2 shown in FIG. 1 is provided with an optical system for forming a 2-dimensional image (fundus image) representing the surface morphology of the fundus Ef of an eye E. Fundus images include observation images, photographed images, etc. The observation image is, for example, a monochromatic moving image formed at a prescribed frame rate using near-infrared light. The photographed image may be, for example, a color image captured by flashing visible light, or a monochromatic still image captured by using near-infrared light or visible light as illumination light. The retinal camera unit 2 may also be configured to be capable of capturing other types of images such as a fluorescein angiography image, an indocyanine green fluorescent image, and an autofluorescent image. It should be noted that a fundus image of any type acquired by the retinal camera unit 2 corresponds to a "front image". Further, the retinal camera unit 2 corresponds to a "photographing part".

The retinal camera unit 2 is provided with a chin rest and a forehead placement for supporting the face of the subject. Moreover, the retinal camera unit 2 is provided with the illumination optical system 10 and the imaging optical system 30. The illumination optical system 10 irradiates illumination light to the fundus Ef. The imaging optical system 30 guides a fundus reflected light of the illumination light to imaging devices (CCD image sensors 35, 38 (sometimes referred to simply as CCD)). Moreover, the imaging optical system 30 guides signal light input from the OCT unit 100 to the fundus Ef, and guides the signal light returned from the fundus Ef to the OCT unit 100.

An observation light source 11 of the illumination optical system 10 comprises, for example, a halogen lamp. Light (observation illumination light) output from the observation light source 11 is reflected by a reflection mirror 12 with a curved reflection surface, and becomes near-infrared after passing through a visible cut filter 14 via a condenser lens 13. Furthermore, the observation illumination light is once converged near an imaging light source 15, reflected by a mirror 16, and passes through relay lenses 17 and 18, a diaphragm 19, and a relay lens 20. Then, the observation illumination light is reflected on the peripheral part (the surrounding region of an aperture part) of an aperture mirror 21, transmitted through a dichroic mirror 46, and refracted by an object lens 22, thereby illuminating the fundus Ef. It should be noted that LED (Light Emitting Diode) may be used as the observation light source.

The fundus reflection light of the observation illumination light is refracted by the object lens 22, transmitted through the dichroic mirror 46, passes through the aperture part formed in the center region of the aperture mirror 21, transmitted through a dichroic mirror 55, travels through a focusing lens 31, and reflected by a mirror 32. Furthermore, the fundus reflection light is transmitted through a half-mirror 39A, refracted by reflected by a dichroic mirror 33, and forms an image on the light receiving surface of the CCD image sensor 35 by a condenser lens 34. The CCD image sensor 35 detects the fundus reflection light at a preset frame rate, for example. An image (observation image) based on the fundus reflection light detected by the CCD image sensor 35 is displayed on a display device 3. It should be noted that when the imaging optical system is focused on the anterior eye part, the observation image of the anterior eye part of the eye E is displayed.

The imaging light source 15 comprises, for example, a xenon lamp. The light (imaging illumination light) output from the imaging light source 15 is irradiated to the fundus Ef via the same route as that of the observation illumination light. The fundus reflection light of the imaging illumination light is guided to the dichroic mirror 33 via the same route as that of the observation illumination light, transmitted through the dichroic mirror 33, reflected by a mirror 36, and forms an image on the light receiving surface of the CCD image sensor 38 by a condenser lens 37. An image (photographed image) based on the fundus reflection light detected by the CCD image sensor 38 is displayed on the display device 3. It should be noted that the display device 3 for displaying the observation image and the display device 3 for displaying the photographed image may be the same or different. Further, when similar photographing is carried out by illuminating the eye E with infrared light, infrared photographed image is displayed. Moreover, LED may be used as the imaging light source.

An LCD (Liquid Crystal Display) 39 displays a fixation target or a target for measuring visual acuity. The fixation target is a visual target for fixating the eye E, and is used when photographing a fundus or performing OCT measurement.

Part of the light output from the LCD 39 is reflected by the half-mirror 39A, reflected by the mirror 32, passes through the aperture part of the aperture mirror 21, refracted by the object lens 22, and projected onto the fundus Ef.

By changing a display position of the fixation target on the screen of the LCD 39, it is possible to change the fixation position of the eye E. Examples of the fixation positions of the eye E include the position for acquiring an image centered at the macula of the fundus Ef, the position for acquiring an image centered at the optic papilla, the position for acquiring an image centered at the fundus center located between the macula and the optic papilla, and so on, as in conventional retinal cameras. Further, the display position of the fixation target may be arbitrarily changed.

Furthermore, as with conventional retinal cameras, the retinal camera unit 2 is provided with an alignment optical system 50 and a focus optical system 60. The alignment optical system 50 generates a target (alignment target) for matching the position (alignment) of the device optical system with respect to the eye E. The focus optical system 60 generates a target (split target) for matching the focus with respect to the eye Ef.

Light (alignment light) output from an LED 51 of the alignment optical system 50 passes through diaphragms 52 and 53 and a relay lens 54, is reflected by the dichroic mirror 55, passes through the aperture part of the aperture mirror 21, is transmitted through the dichroic mirror 46, and is projected onto the cornea of the eye E by the object lens 22.

Cornea reflection light of the alignment light passes through the object lens 22, the dichroic mirror 46 and the aperture part, a part of the cornea reflection light is transmitted through the dichroic mirror 55, passes through the focusing lens 31, reflected by the mirror 32, transmitted through the half-mirror 39A, reflected by the dichroic mirror 33, and projected onto the light receiving surface of the CCD image sensor 35 by the condenser lens 34. An image (alignment target) captured by the CCD image sensor 35 is displayed on the display device 3 together with the observation image. The user conducts alignment by an operation that is the same as conventional retinal cameras. Further, alignment may be performed in a way in which the arithmetic and control unit 200 analyzes the position of the alignment target and controls the movement of the optical system (automatic alignment function).

In order to conduct focus adjustment, the reflection surface of a reflection rod 67 is positioned at a slanted position on the optical path of the illumination optical system 10. Light (focus light) output from an LED 61 of the focus optical system 60 passes through a relay lens 62, is split into two light fluxes by a split target plate 63, passes through a two-hole diaphragm 64, is reflected by a mirror 65, and is reflected after an image is formed once on the reflection surface of the reflection rod 67 by a condenser lens 66. Furthermore, the focus light passes through the relay lens 20, is reflected at the aperture mirror 21, is transmitted through the dichroic mirror 46, is refracted by the object lens 22, and is projected onto the fundus Ef.

The fundus reflection light of the focus light passes through the same route as the cornea reflection light of the alignment light and is detected by the CCD image sensor 35. An image (split target) captured by the CCD image sensor 35 is displayed on the display device 3 together with the observation image. The arithmetic and control unit 200, as in the conventional technology, analyzes the position of the split target, and moves the focusing lens 31 and the focus optical system 60 for focusing (automatic focusing function). Further, focusing may be performed manually while visually recognizing the split target.

The dichroic mirror 46 splits the optical path for OCT from the optical for eye fundus photographing. The dichroic mirror 46 reflects light of the wavelength band used for OCT, and transmits the light for eye fundus photographing. The optical path for OCT is provided with a collimator lens unit 40, an optical path length changing part 41, a galvano scanner 42, a focusing lens 43, a mirror 44 and a relay lens 45.

The optical path length changing part 41 is capable of moving in the direction indicated by the arrow in FIG. 1 to change the length of the optical path for OCT. This change of optical path length may be used for correction of the optical path length in accordance with the axial length of the eye E, and for adjustment of the condition of interference. The optical path length changing part 41 is configured to comprise a corner cube and a mechanism for moving the corner cube, for example.

The galvano scanner 42 changes the travelling direction of light (signal light LS) travelling along the optical path for OCT. Thereby, the fundus Ef is scanned by the signal light LS. The galvano scanner 42 is configured to comprise a galvano mirror for scanning with the signal light LS in the x-direction, a galvano mirror for scanning in the y-direction, and a mechanism for independently driving these. Thereby, the signal light LS may be scanned in an arbitrary direction in the xy-plane.

[OCT Unit]

An example of the configuration of the OCT unit 100 is explained while referring to FIG. 2. The OCT unit 100 is provided with an optical system for obtaining an OCT image of the fundus Ef. The optical system comprises a similar configuration to a conventional Spectral Domain OCT apparatus. That is to say, this optical system is configured to split low-coherence light into signal light and reference light, superpose the signal light returned form the fundus Ef and the reference light having traveled through a reference optical path to generate interference light, and detect the spectral components of the interference light. This detection result (detection signal) is transmitted to the arithmetic and control unit 200.

It should be noted that when Swept Source OCT apparatus is used, a swept source is provided instead of a low-coherence light source while an optical member for spectrally decomposing interference light is not provided. In general, any known technology in accordance with the type of OCT may be arbitrarily applied for the configuration of the OCT unit 100.

A light source unit 101 outputs broadband low-coherence light L0. The low-coherence light L0, for example, includes near-infrared wavelength band (about 800-900 nm) and has a coherence length of about tens of micrometer. Moreover, it is possible to use, as the low-coherence light L0, near-infrared light having wavelength band that is impossible to be detected by human eyes, for example, infrared light having the center wavelength of about 1040-1060 nm.

The light source unit 101 is configured to comprise light output device, such as an SLD (super luminescent diode), LED, SOA (Semiconductor Optical Amplifier) and the like.

The low-coherence light L0 output from the light source unit 101 is guided to a fiber coupler 103 by an optical fiber 102 and split into the signal light LS and the reference light LR.

The reference light LR is guided to an optical attenuator 105 by an optical fiber 104. Through any known technology, the optical attenuator 105 received control of the arithmetic and control unit 200 for automatically adjusting light amount (light intensity) of the reference light LR guided to the optical fiber 104. The reference light LR having adjusted by the optical attenuator 105 is guided to a polarization controller 106 by the optical fiber 104. The polarization controller 106 is a device configured to, for example, apply stress to the loop-form optical fiber 104 from outside to adjust polarization condition of the reference light LR being guided in the optical fiber 104. It should be noted that the configuration of the polarization controller 106 is not limited to this, and arbitrary known technology may be applied. The reference light LR whose polarization condition has been adjusted by the polarization controller 106 is guided to an optical coupler 109.

The signal light LS generated by the fiber coupler 103 is guided by the optical fiber 107, and converted into a parallel light flux by the collimator lens unit 40. Further, the signal light LS travels through the optical path length changing part 41, the galvano scanner 42, the focusing lens 43, the mirror 44 and the relay lens 45, and reaches the dichroic mirror 46. Further, the signal light LS is reflected by the dichroic mirror 46, refracted by the objective lens 22, and projected to the fundus Ef. The signal light LS is scattered (including reflection) at various depth positions of the fundus Ef. The back-scattered light of the signal light LS from the fundus Ef travels along the same route as the outward way in the opposite direction to the fiber coupler 103, and is reached the fiber coupler 109 through an optical fiber 108.

The fiber coupler 109 superposes the back-scattered light of the signal light LS and the reference light LR having passed through the optical fiber 104. Interference light LC thus generated is guided by an optical fiber 110 and output from an exit end 111. Furthermore, the interference light LC is converted into a parallel light flux by a collimator lens 112, spectrally divided (spectrally decomposed) by a diffraction grating 113, converged by a condenser lens 114, and projected onto the light receiving surface of a CCD image sensor 115. It should be noted that although the diffraction grating 113 shown in FIG. 2 is of transmission type, any other kind of a spectrally decomposing element (such as reflection type) may be used.

The CCD image sensor 115 is for example a line sensor, and detects the respective spectral components of the spectrally decomposed interference light LC and converts the components into electric charges. The CCD image sensor 115 accumulates these electric charges, generates a detection signal, and transmits the detection signal to the arithmetic and control unit 200.

Although a Michelson-type interferometer is employed in the present embodiment, it is possible to employ any type of interferometer such as a Mach-Zehnder-type as necessary. Instead of a CCD image sensor, other types of image sensors, such as a CMOS (Complementary Metal Oxide Semiconductor) image sensor, may be used.

[Arithmetic and Control Unit]

A configuration of the arithmetic and control unit 200 will be described. The arithmetic and control unit 200 analyzes the detection signals input from the CCD image sensor 115 to form an OCT image of the fundus Ef. Arithmetic processing for this may be the same as that of a conventional Spectral Domain OCT apparatus.

Further, the arithmetic and control unit 200 controls each part of the retinal camera unit 2, the display device 3 and the OCT unit 100. For example, the arithmetic and control unit 200 displays an OCT image of the fundus Ef on the display device 3.

Further, as controls of the retinal camera unit 2, the arithmetic and control unit 200 executes: controls of actions of the observation light source 101, the imaging light source 103 and LED's 51 and 61; control of action of the LCD 39; controls of movements of the focusing lenses 31 and 43; control of movement of the reflection rod 67; control of movement of the focus optical system 60; control of movement of the optical path length changing part 41; control of action of the galvano scanner 42; and so on.

Further, as controls of the OCT unit 100, the arithmetic and control unit 200 executes: control of action of the light source unit 101; control of action of the optical attenuator 105; control of action of the polarization controller 106; control of action of the CCD image sensor 115; and so on.

The arithmetic and control unit 200 comprises a microprocessor, a RAM, a ROM, a hard disk drive, a communication interface, and so on, as in conventional computers. The storage device such as the hard disk drive stores a computer program for controlling the ophthalmologic imaging apparatus 1. The arithmetic and control unit 200 may be provided with various circuit boards such as a circuit board for forming OCT images. Moreover, the arithmetic and control unit 200 may be provided with operation devices (input devices) such as a keyboard, a mouse, etc. and/or a display device such as an LCD etc.

The retinal camera unit 2, the display device 3, the OCT unit 100, and the arithmetic and control unit 200 may be integrally configured (that is, provided within a single case), or separately configured in two or more cases.

[Control System]

Figure 3:
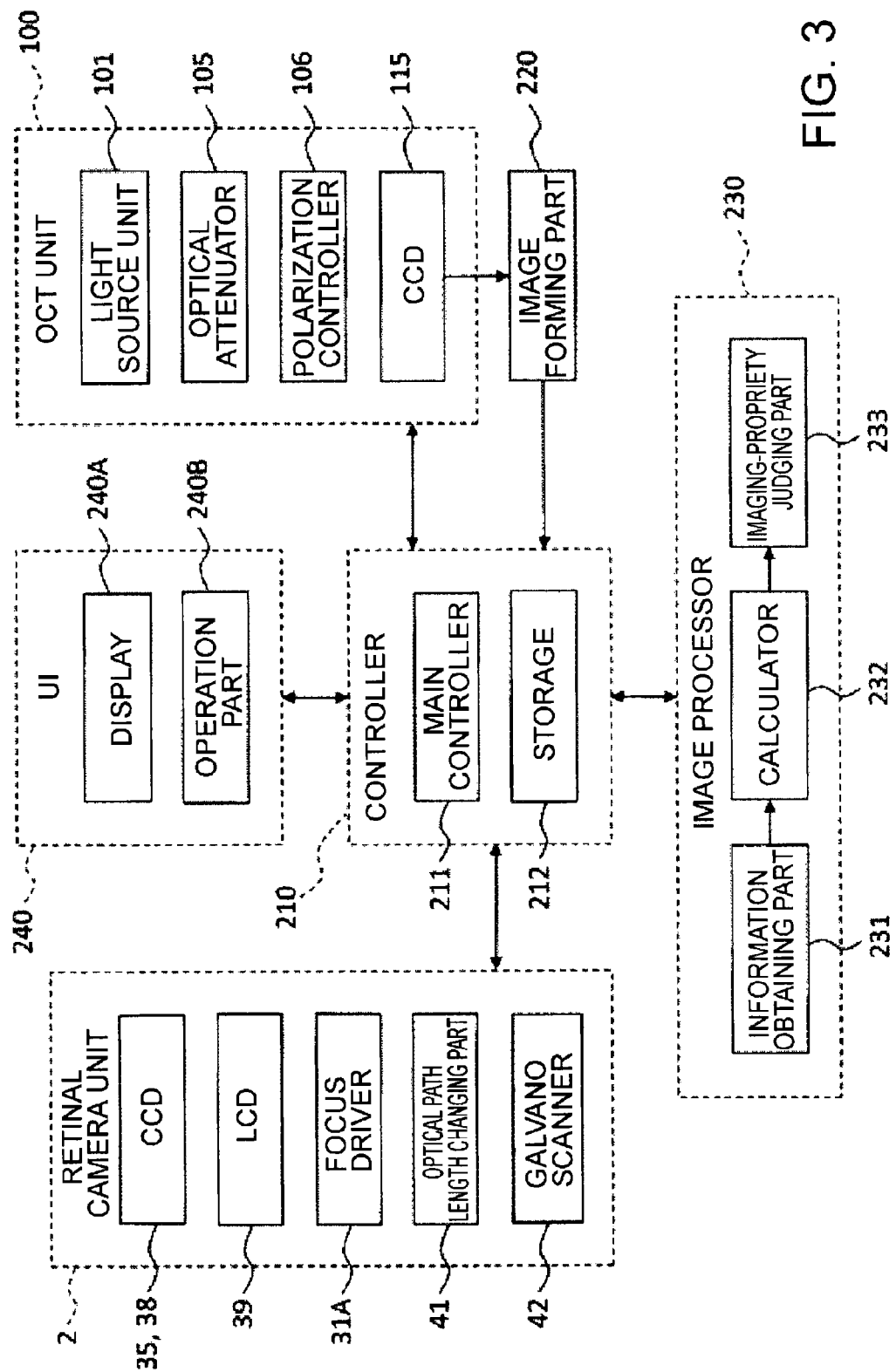
FIG. 3 is a schematic block diagram showing an example of a configuration of an ophthalmologic imaging apparatus according to an embodiment.
Figure 4:
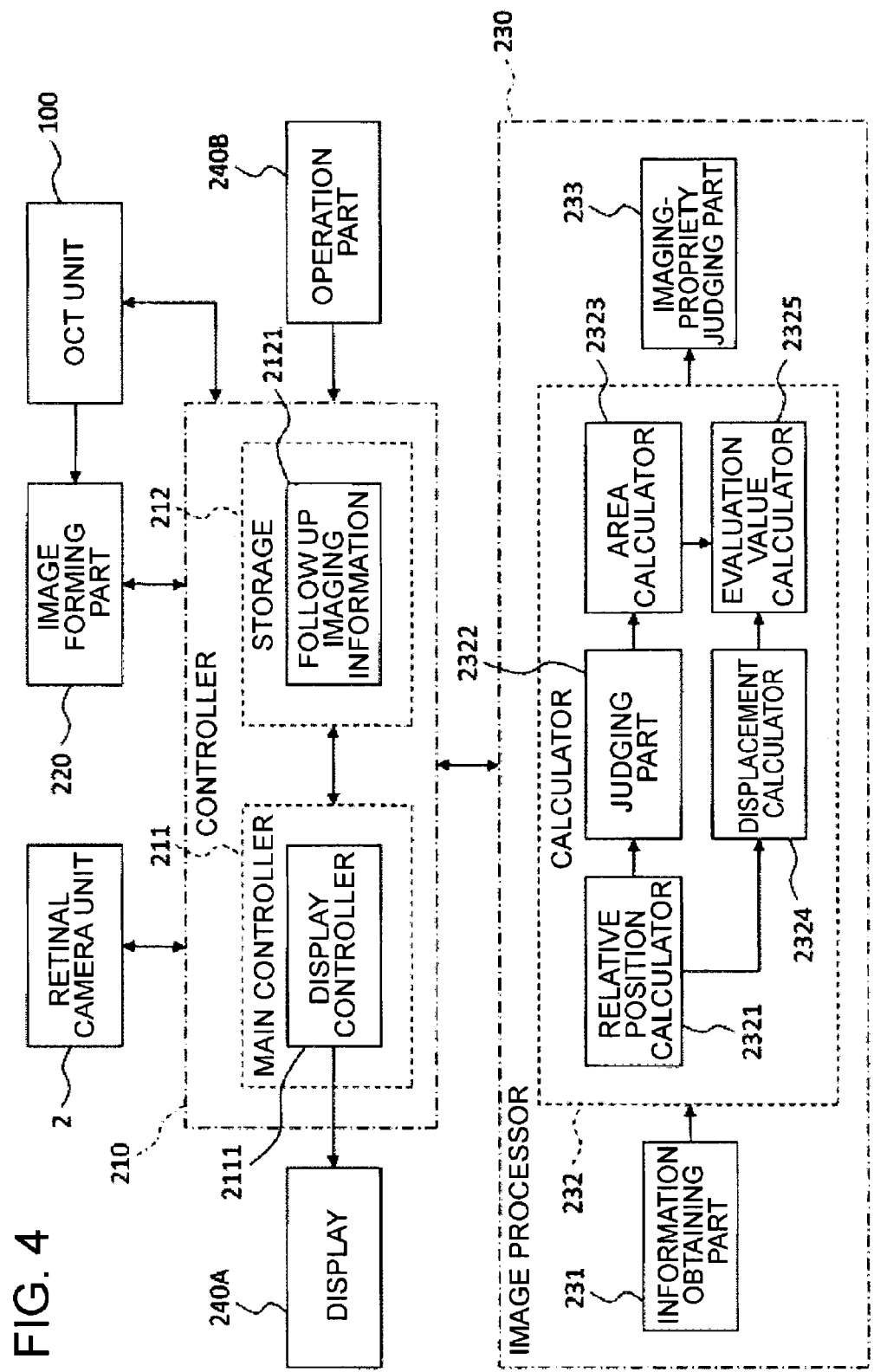
FIG. 4 is a schematic block diagram showing an example of a configuration of an ophthalmologic imaging apparatus according to an embodiment.

A configuration of a control system of the ophthalmologic imaging apparatus 1 will be described with reference to FIGS. 3 and 4.

Now, the ophthalmologic imaging apparatus 1 is configured to be capable of executing follow up imaging and post-processing thereof. The follow up imaging is an imaging technique for acquiring a cross sectional image by referring to a front image of an eye acquired in the past and scanning the same position as before with light. Further, the post-processing includes processing of evaluating an error in scanning positions of light in the follow up imaging. In other words, the post-processing includes processing of evaluating the gap (misregistration) between a scanning position in the past imaging and a scanning position in the follow up imaging based on a front image acquired in this past imaging. It should be noted that the ophthalmologic image processing apparatus according to embodiments carries out such post-processing.

Before explaining the control system, follow up imaging will be explained briefly. In follow up imaging, controls of respective parts of the ophthalmologic imaging apparatus 1 are executed by the controller 210 (in particular, the main controller 211).

Follow up imaging is an imaging method of reproducing a scanning position applied in the past imaging and performing the present imaging. In a preparatory phase thereof, a patient selecting screen (illustration omitted) is displayed on the display 240A. The patient selecting screen is provided with: a function for selecting a patient who becomes a subject of follow up imaging (patient selecting part); a function for displaying patient information (patient information display); and a function for displaying imaging information (imaging information display). Further, the patient selecting screen is provided with various operation parts (software keys).

The patient selecting part includes a space for inputting a retrieval query, calendar for selecting a date of imaging (such as the date of the last imaging in the past), etc. Once information is input into the patient selecting part, the controller 210 searches patient information stored in an information storage (the storage 212 of the ophthalmologic imaging apparatus 1, database on a network, etc.), and displays the search result on the patient information display. Such information displayed may include a patient ID, patient name, sex, date of birth, etc. It should be noted that when a date of imaging is selected from the calendar and the like, a plurality of patient information are listed in the patient information display. In such a case, the user may select a desired patient from among the plurality of patient information.

Once one patient is selected, the controller 210 obtains imaging information relating to this patient and displays it on the imaging information display. If imaging has been carried out a plurality of times in the past, a plurality of imaging information relating to the plurality of imaging are listed in chronological order. The imaging information may include the date of imaging, time of imaging, data storage destination (file address etc.), information whether or not this is follow up imaging, scanning mode of OCT measurement (described later), identification information of left/right eye(s), fixation position, information relating to analysis (retinal thickness analysis etc.), and so on.

Once the user selects imaging information as a reference in the present follow up imaging, the controller 210 obtains image data acquired by imaging corresponding to the selected imaging information from the information storage, and displays images based on the image data (front image and cross sectional image) on the display 240A. Here, display screen is switched from the patient selecting screen to an image display screen (illustration omitted). The user observes the displayed images and determines whether to carry out follow up imaging by referring to the front image. If other front images are referred to, other images acquired by this imaging or images acquired by other imaging are displayed and similar determination is carried out. Once the user determines a referred front image, the controller 210 displays this front image (reference front image, or first front image) on the display 240A, and control status is transferred to waiting status for a command of commencing follow up imaging.

Once a predetermined imaging-commencing command is input, the controller 210 acquires near-infrared moving image of the eye E in real time. Then, the controller 210 executes image matching between frames of this near-infrared moving image (second front image, or follow-up front image) and the reference front image while performing tracking (described later), and executes OCT measurement with the same scanning mode as the past imaging. This OCT measurement is started at a timing at which tracking is carried out properly, for example. Further, scanning with the same scanning mode is repeated a predetermined times in this OCT measurement. An image forming part 220 averages multiple image data acquired in this repeating scanning to form a final image.

Image data of OCT images acquired from such follow up imaging are associated with patient information, scanning position information of this follow up imaging, frames of near-infrared moving image acquired in this follow up imaging, imaging information of this follow up imaging, information relating to referred past imaging (scanning position information, imaging information, image data, etc.), and stored in the storage 212. Here, the frames of near-infrared moving image to be stored are frames acquired first and last in the period in which OCT measurement is carried out, for example.

This is the end of the explanation of processing executed in follow up imaging and explanation of the control system starts again.

(Controller)

The control system of the ophthalmologic imaging apparatus 1 has a configuration centered on a controller 210. The controller 210 is configured to comprise, for example, the aforementioned microprocessor, RAM, ROM, hard disk drive, and communication interface, etc. The controller 210 is provided with a main controller 211 and storage 212.

(Main Controller)

The main controller 211 performs the aforementioned various kinds of controls. Specifically, the main controller 211 controls a focus driver 31A, the optical path length changing part 41 and the galvano scanner 42 of the retinal camera unit 2, and further controls the light source unit 101, the optical attenuator 105 and the polarization controller 106 of the OCT unit 100.

The focus driver 31A moves the focusing lens 31 in the direction of the optical axis. Thereby, the focus position of the imaging optical system 30 is changed. It should be noted that the main controller 211 may control an optical system driver (not shown in diagrams) to three dimensionally move the optical system provided in the retinal camera unit 2. This control is used for alignment and tracking. Tracking is an operation for move the optical system in accordance with eye movement of the eye E. When tracking is applied, alignment and focusing are carried out in advance. Tracking is a function to maintain adequate positional relationship in which alignment and focusing are matched by causing the position of the optical system to follow the eye movement.

The main controller 211 executes a process of writing data into the storage 212, and a process of reading out data from the storage 212. The main controller 211 includes a display controller 2111 that displays various information on the display 240A. The display controller 2111 functions as an example of a "first display part" and "second display part". Processing executed by the display controller 2111 is described later.

(Storage)

The storage 212 stores various kinds of data. The data stored in the storage 212 may include image data of OCT images, image data of fundus images, and eye information, for example. The eye information includes information on the eye, such as information on a subject such as a patient ID and a name, identification information on left eye or right eye, and so on. Further, the storage 212 stores various programs and data for operating the ophthalmologic imaging apparatus 1.

The storage 212 stores follow up imaging information 2121. The follow up imaging information 2121 is information relating to follow up imaging carried out in the past. The follow up imaging information 2121 includes at least: front images of the eye E referred to in follow up imaging carried out in the past (first front image, or reference front image); and front images of the eye E acquired in this follow up imaging (second front image, or follow-up front image). The latter front images are frames of near-infrared moving image acquired in real time in this follow up imaging. The frames are frames acquired first and last in the period in which OCT measurement is carried out.

Further, the follow up imaging information 2121 may include reference scanning position information indicating scanning position (first scanning position, or reference scanning position) of a cross sectional image formed together with the reference front image; and follow-up scanning position information indicating scanning position (second scanning position, or follow-up scanning position) of a cross sectional image acquired together with the follow-up front image. These scanning position information include control information of the galvano scanner 42 in the scanning, that is, information indicating directions of the galvano scanner 42, for example. Further, if front images are being acquired in real time during OCT measurement, the scanning position information may include coordinates of scanning position (scanning locus) depicted in the front images.

(Image Forming Part)

The image forming part 220 forms image data of a cross sectional image of the fundus Ef based on the detection signals from the CCD image sensor 115. Like conventional Spectral Domain OCT, this process includes processes such as noise elimination (noise reduction), filtering and FFT (Fast Fourier Transform).

When scanning is carried out predetermined times in succession with the same scanning mode, the image forming part 220 executes processing of forming new image data by superposing image data of multiple cross sectional images acquired from this successive scanning. This superposition is carried out for the purpose of eliminating random noises mixed in image data.

In the case in which other OCT type is applied, the image forming part 220 executes known processing in accordance with the applied OCT type. The image forming part 220 is configured to include the aforementioned circuit board, for example. The image forming part 220 functions as a "cross sectional image forming part" together with an optical system used for OCT measurement. It should be noted "image data" and an "image" based on the image data may be identified with each other in the description.

(Image Processor)

An image processor 230 executes various image processing and analysis processing on OCT images formed by the image forming part 220. For example, the image processor 230 executes various correction processing such as brightness correction, dispersion correction of images, etc. Moreover, the image processor 230 analyzes OCT images to perform layer thickness analysis for obtaining retinal thickness distribution. Further, the image processor 230 executes various image processing and analysis processing on images obtained by the retinal camera unit 2 (fundus images, anterior eye part images, etc.).

The image processor 230 executes known image processing such as interpolation processing for interpolating pixels between cross sectional images to form image data of a three-dimensional image of the fundus Ef. It should be noted that the image data of a three-dimensional image refers to image data that the positions of pixels are defined by the three-dimensional coordinates. The image data of a three-dimensional image is, for example, image data composed of three-dimensionally arranged voxels. This image data is referred to as volume data, voxel data, or the like. For displaying an image based on the volume data, the image processor 230 executes a rendering process (such as volume rendering and MIP (Maximum Intensity Projection)) on this volume data, and forms image data of a pseudo three-dimensional image taken from a specific view direction. On a display device such as a display 240A, this pseudo three-dimensional image is displayed.

Further, it is also possible to form stack data of multiple cross sectional images as the image data of a three-dimensional image. Stack data is image data obtained by three-dimensionally arranging multiple cross sectional images obtained along multiple scanning lines, based on the positional relation of the scanning lines. That is to say, stack data is image data obtained by expressing multiple cross sectional images defined by originally individual two-dimensional coordinate systems by a three-dimensional coordinate system (in other words, embedding into a three-dimensional space).

The image processor 230 includes an information obtaining part 231, calculator 232 and imaging-propriety judging part 233. They execute post-processing of follow up imaging. The post-processing evaluates an error in scanning position of light in follow up imaging as described above.

(Information Obtaining Part)

The information obtaining part 231 analyzes a front image referred to in follow up imaging (reference front image) and a front image acquired in the follow up image (follow-up front image) to obtain misregistration information between these front images. The misregistration information quantitatively expresses how much the depicted position of morphology of the fundus Ef in these front images is shifted.

As the misregistration information, the information obtaining part 231 calculates a parallel shift error and rotational shift error between the reference front image and follow-up front image, for example. The parallel shift error corresponds to a displacement, in a spreading directions of front images (that is, in the xy-plane), of morphology of the fundus Ef depicted in these front images. The rotational shift error corresponds to a displacement of the morphology in a rotational direction centered at a certain position in the xy-plane. It should be noted that the parallel shift error and rotational shift error are expressed as an affine transformation between coordinates of both front images, for example. Further, it may be configured to calculate any one of the parallel shift error and rotational shift error.

An example of method of calculating the parallel shift error and rotational shift error is explained. Firstly, the information obtaining part 231 analyzes the respective front images to specify image positions corresponding to a predetermined characteristic site of the fundus Ef. The characteristic site is, for example, the center/edge of an optic disk, center of a macula, specific blood vessel, branch point of a blood vessel, lesion site, etc.

Next, the information obtaining part 231 obtains a displacement between the coordinates of the image point in the reference front image and the coordinates of the image point in the follow-up front image. This processing determines, for each of the image positions of multiple characteristic sites, components of an affine transformation matrix by substituting the coordinates of the image positions in the both front images into the known formula of two-dimensional affine transformation, for example. It should be noted that the coordinates of the image positions are address information assigned to the respective pixels in advance. The affine transformation matrix obtained in this way includes both information of the parallel shift error and rotational shift error between the front images.

(Calculator)

The calculator 232 calculates an evaluation value of an error in a scanning position in follow up imaging based on the misregistration information obtained by the information obtaining part 231. Examples of the evaluation value include: an evaluation value calculated based on an area of a preset image region defined by the scanning position relating to the reference front information and the scanning position relating to the follow-up front information; and an evaluation value calculated based on a displacement between these scanning positions. It should be noted that an evaluation value may be calculated based on a factor(s) other than these. Further, an evaluation value may be calculated by combining different factors.

The calculator 232 includes a relative position calculator 2321, judging part 2322, area calculator 2323, displacement calculator 2324 and evaluation value calculator 2325. Calculation of an evaluation value based on the area is carried out by the relative position calculator 2321, judging part 2322 and area calculator 2323. Calculation of an evaluation value based on the displacement is carried out by the relative position calculator 2321, displacement calculator 2324 and evaluation value calculator 2325.

(Relative Position Calculator)

As described above, the follow up imaging information 2121 stored in the storage 212 includes the reference scanning position information and the follow-up scanning position information. The relative position calculator 2321 calculates relative position information between the reference scanning position information and the follow-up scanning position information based on the misregistration information obtained by the information obtaining part 231.

Now, follow up imaging is an imaging method in which a past scanning position is reproduced and OCT measurement is carried out. Thus, in an ideal case, the reference scanning position and the follow-up scanning position coincide with each other. However, in reality, it is difficult to completely reproduce scanning position due to involuntary eye movement during fixation etc. On the other hand, since the reference scanning position and the follow-up scanning position coincide with each other if involuntary eye movement during fixation etc. is not involved, the relative position between these scanning positions corresponds to misregistration (displacement) of the eye E due to involuntary eye movement during fixation etc., that is, corresponds to misregistration between the reference scanning position and the follow-up scanning position. This misregistration is obtained as the misregistration information by the information obtaining part 231.

The relative position calculator 2321, for example, displaces the reference scanning position by an amount of misregistration indicated in the misregistration information to obtain a position corresponding to the reference scanning position in the follow-up front image, that is, to obtain an ideal scanning position realized in a case in which the reference scanning position is completely reproduced. The relative position information indicates the relative position between this ideal scanning position and the scanning position applied in the actual follow up imaging (follow-up scanning position). In this way, the relative position information and the misregistration information are substantially equivalent. Specifically, the misregistration information indicates a displacement between the front images while the relative position information indicates a displacement between the scanning positions. The relative position calculator 2321 sends the obtained relative position information to the judging part 2322 and the displacement calculator 2324.

(Judging Part)

Figure 5A:
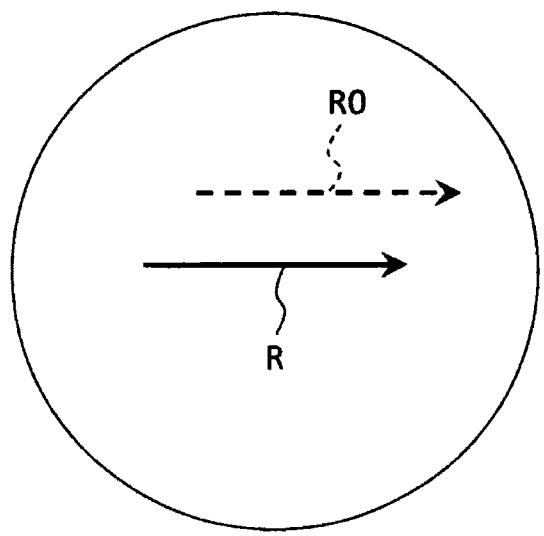
FIG. 5A is a schematic diagram for explaining an operation of an ophthalmologic imaging apparatus according to an embodiment.
Figure 5B:
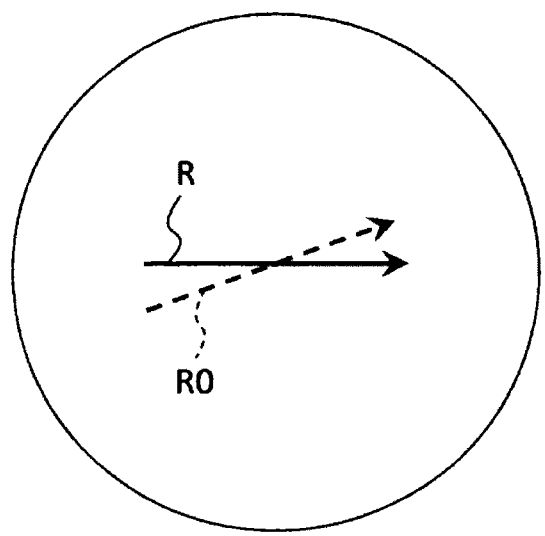
FIG. 5B is a schematic diagram for explaining an operation of an ophthalmologic imaging apparatus according to an embodiment.
Figure 5C:
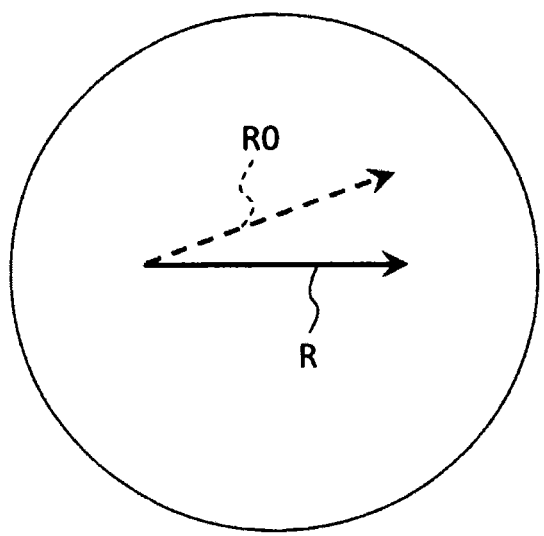
FIG. 5C is a schematic diagram for explaining an operation of an ophthalmologic imaging apparatus according to an embodiment.
Figure 5D:
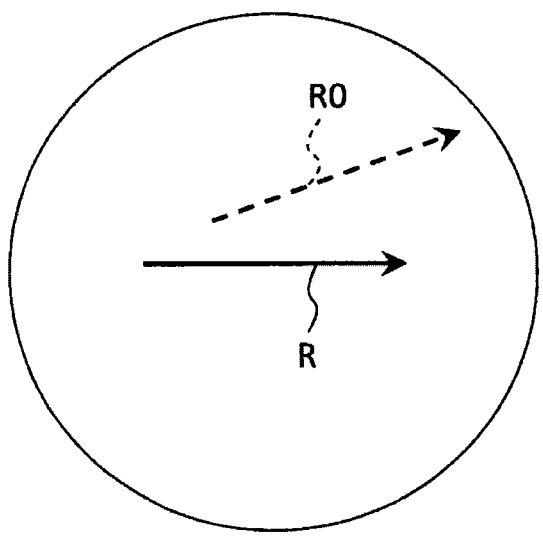
FIG. 5D is a schematic diagram for explaining an operation of an ophthalmologic imaging apparatus according to an embodiment.

FIGS. 5A to 5D illustrate examples of aspects of the relative position between the reference scanning position and the follow-up scanning position. In these diagrams, a symbol R indicates the follow-up scanning position in the follow-up front image. Further, a symbol R0 indicates the reference scanning position in the follow-up front image, that is, the reference scanning position displaced based on the misregistration information (the relative position information). FIG. 5A indicates an example of a case in which only the parallel shift error is involved. FIG. 5B indicates an example of a case in which only the rotational shift error is involved and both scanning positions intersects with each other near their centers. FIG. 5C indicates an example of a case in which only the rotational shift error is involved and both scanning positions intersects with each other near their scanning start positions. FIG. 5D indicates an example of a case in which both the parallel shift error and the rotational shift error are involved. It should be noted that aspects of relative positions of the scanning positions are not limited to these. Further, scanning modes are not limited to the line scan.

The judging part 2322 judges whether or not the reference scanning position and the follow-up scanning position have a common position based on the misregistration information (the relative position information). The common position indicates a position (a region) in which the reference scanning position and the follow-up scanning position are overlapped with each other.

The common position is a zero-dimensional region (a point), one-dimensional region (a line), or two-dimensional region (a plane). In FIGS. 5A to 5D, since both of the reference scanning position and the follow-up scanning position are of a line-segment shape, the common position becomes an intersection point when they intersect with each other and no common position exist when they do not intersect. Further, although illustration is omitted, if the direction of displacement between the reference scanning position and the follow-up scanning position is only the length direction and the amount of the displacement is less than the length, then the common position of these two scanning positions becomes a one-dimensional region. Further, when three-dimensional scan is used as scanning mode, both of the reference scanning position and the follow-up scanning position become two-dimensional regions, and the common position of these becomes a zero, one or two-region in accordance with relative positional relationship.

Judgment whether or not the common position exists is carried out based on the coordinates of the reference scanning position and the coordinates of the follow-up scanning position in the follow-up front image. For example, the judging part 2322 collates the coordinates of the reference scanning position with the coordinates of the follow-up scanning position, and judges the common position exists if the common coordinates exist between these scanning positions and judges the common position does not exist if the common coordinates does not exist. From this processing, the coordinates of the common position in the follow-up front image are also obtained. It should be noted that these coordinates are coordinates in a two-dimensional coordinate system defined for the follow-up front image.

The judging part 2322 sends the judgment result relating to the common position (presence/absence of the common position, coordinates of the common position, etc.) to the area calculator 2323.

(Area Calculator)

The area calculator 2323 calculates an area of an image region defined by the reference scanning position and the follow-up scanning position based on the misregistration information (relative position information). Here, the misregistration information and the relative position information are substantially equivalent. Further, the image region whose area is to be calculated is a partial region of the follow-up front image. Further, a method of defining the image region from the two scanning positions is predetermined. Further, processing of calculating the area may be carried out in an arbitrary way. The processing of calculating the area may include, for example, processing of counting the number of pixels in the image region, processing of deriving a mathematical expression (an equation etc.) expressing the boundary of the image region, or integration, or the like. Further, the area, that is the result of calculation, may be a numerical value uniquely expressing the two-dimensional size of the image region.

The area calculator 2323 executes different arithmetic processing in accordance with the judgment result from the judging part 2322. For example, the area calculator 2323 executes one arithmetic processing when the reference scanning position and the follow-up scanning position have the common position and another arithmetic processing when they do not. Hereinafter, specific examples thereof are explained. The following specific examples treat cases in which two scanning positions are of a line-segment shape, and consider cases in which these scanning positions intersect and cases in which they do not separately. That is, cases in which the common position exists and cases in which it does not are considered separately. Further, regarding cases in which two scanning positions intersect with each other, cases in which the intersection point is located at an endpoint and cases in which it is located at other point are considered separately. Judgment whether or not the intersection point is located at an endpoint may be easily carried out based on the coordinates of the two scanning positions and the coordinates of the intersection point. It should be noted that the endpoints of the scanning position indicates the scanning start point and the scanning end point of the scanning position of a line-segment shape. Further, the scanning positions are of a line-segment shape and so there exists only one intersection point in the following specific examples; however, when the scanning position is of a curved shape there are cases in which two or more intersection points exist.

When two scanning positions intersect as indicated in FIGS. 5B and 5C, the area calculator 2323 calculates the area of the image region defined by the endpoints of the two scanning positions and the intersection point. More specifically, the area calculator 2323 calculates a sum of an area of a triangle formed by the intersection point and the end points of the two scanning positions located on one side from the intersection point and an area of a triangle formed by the intersection point and the end points of the two scanning positions located on the other side.

Figure 6A:
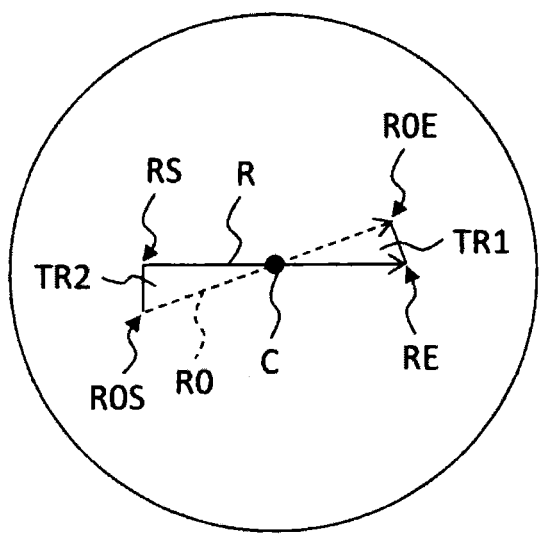
FIG. 6A is a schematic diagram for explaining an operation of an ophthalmologic imaging apparatus according to an embodiment.
Figure 6B:
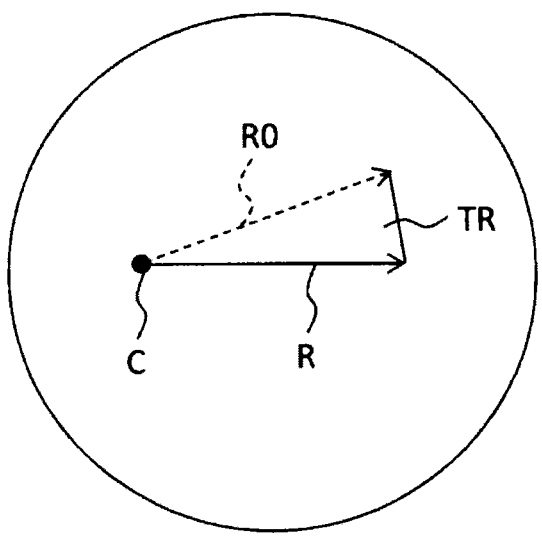
FIG. 6B is a schematic diagram for explaining an operation of an ophthalmologic imaging apparatus according to an embodiment.

For example, when the intersection point is located at a position other than the endpoints of the scanning positions as illustrated in FIG. 5B, the area calculator 2323 calculates, as shown in FIG. 6A, the area of the triangle TR1 having the endpoints (scanning end points) R0E and RE of the two scanning positions R0 and R located on the right side of the intersection point C and the intersection point C as vertices thereof. Further, the area calculator 2323 calculates the area of the triangle TR2 having the endpoints (scanning start points) R0S and RS of the two scanning positions R0 and R located on the left side of the intersection point C and the intersection point C as vertices thereof. Then, the area calculator 2323 adds the area of the triangle TR1 to the area of the triangle TR2. This sum is an objective value of an area.

As another example, when the two scanning positions intersect at the endpoints (scanning start points) as illustrated in FIG. 5C, the area calculator 2323 calculates the area of the triangle TR having the intersection point C (both scanning start points), the scanning end point of the reference scanning position R0 and the scanning end point of the follow-up scanning position R as vertices thereof.

It should be noted that when the two scanning positions intersect at an endpoint of one scanning position and a point of the other scanning position other than its endpoints, it is possible to calculate, for example, the area of the triangle having the intersection point, the opposite endpoint of one scanning position and one endpoint of the other scanning position (such as an endpoint located on the same side as this opposite endpoint) as vertices thereof.

Figure 6C:
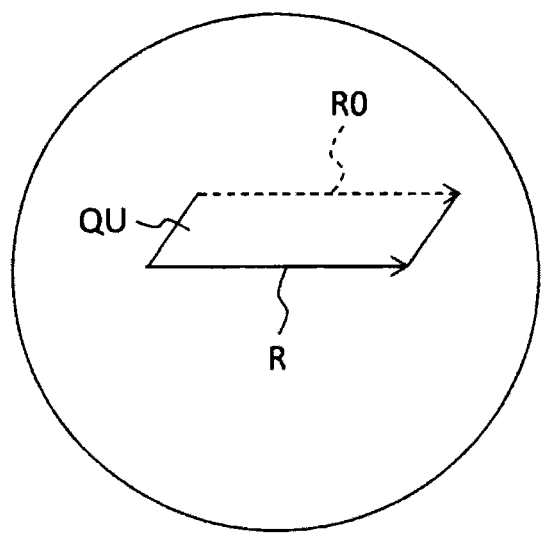
FIG. 6C is a schematic diagram for explaining an operation of an ophthalmologic imaging apparatus according to an embodiment.
Figure 6D:
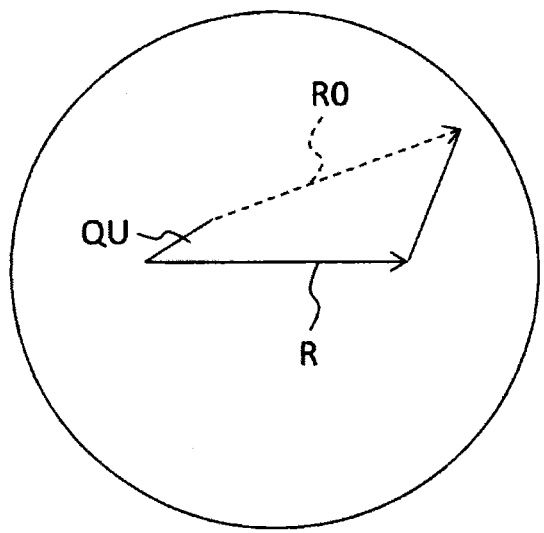
FIG. 6D is a schematic diagram for explaining an operation of an ophthalmologic imaging apparatus according to an embodiment.

On the other hand, when two scanning positions do not intersect as illustrated in FIGS. 5A and 5D, the area calculator 2323 calculates the area of a quadrangle defined by the two scanning positions and sets it as the target area of image region. More specifically, when two scanning positions do not intersect, the area calculator 2323 calculates, as illustrated in FIGS. 6C and 6D, the area of a quadrangle QU having the reference scanning position R0 and the follow-up scanning position R as two sides and two line segments connecting endpoints of these scanning positions as other two sides.

The area calculator 2323 sends the area obtained in the above fashion to the evaluation value calculator 2325.

(Displacement Calculator)

The displacement calculator 2324 calculates a displacement between the reference scanning position and the follow-up scanning position based on the misregistration information (the relative position information). Ways of calculating the displacement are arbitrary. Hereinafter, specific examples of the displacement calculation are explained with referring to FIG. 7.

Figure 7:
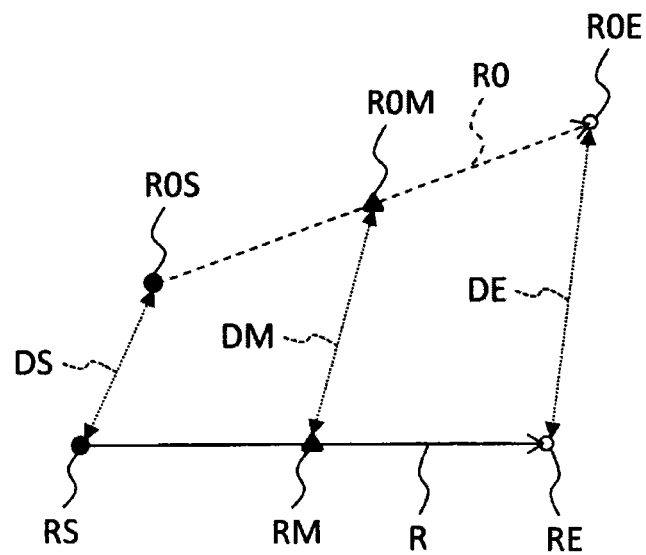
FIG. 7 is a schematic diagram for explaining an operation of an ophthalmologic imaging apparatus according to an embodiment.

FIG. 7 illustrates the reference scanning position R0 and the follow-up scanning position R, each of which is of a line-segment shape. It should be noted that calculation of the displacement may be carried out regardless of the fact whether or not the two scanning positions intersect.

The displacement calculator 2324 firstly specifies predetermined positions on the respective scanning positions R0 and R. This specification processing may be carried out based on the coordinates of the respective points of the scanning positions R0 and R of a line-segment shape. Examples of the predetermined position include a scanning start point, scanning end point, middle point, etc. It should be noted that when scanning positions of a shape other than line-segment shape are considered, it is possible to apply in accordance with the shape. Further, predetermined positions of the same type may be applied for two scanning positions which are to be compared. For example, when a scanning start point is used as the predetermined position, both scanning start points may be specified. Further, when multiple types of predetermined positions are specified, the respective predetermined positions are associated with its type.

Next, the displacement calculator 2324 calculates the displacement between the coordinates of the predetermined position in the reference scanning position R0 and the coordinates of the predetermined position in the follow-up scanning position R. This calculation may be carried out by using a two-dimensional coordinate system previously defined for the follow-up front image. Further, the displacement may be calculated by counting the number of pixels located between the two predetermined positions. The displacement calculated here is a displacement between the predetermined positions the same type. For example, this displacement is a displacement between two scanning start points and not a displacement between a scanning start point and a middle point.

FIG. 7 illustrates a case in which three types (scanning start points, scanning end points and middle points) are applied as the abovementioned predetermined positions. In FIG. 7, a symbol DS indicates a displacement between the scanning start point R0S of the reference scanning position R0 and the scanning start point RS of the follow-up scanning position R. Further, a symbol DE indicates a displacement between the scanning end point R0E of the reference scanning position R0 and the scanning end point RE of the follow-up scanning position R. Further, a symbol DM indicates a displacement between the middle point R0M of the reference scanning position R0 and the middle point RM of the follow-up scanning position R.

The displacement calculator 2324 sends the displacement calculated in such a way to the evaluation value calculator 2325.

(Evaluation Value Calculator)

The evaluation value calculator 2325 calculates an evaluation value of an error in the scanning position applied in the follow up imaging. The information of area obtained by the area calculator 2323 and the information of displacement obtained by the displacement calculator 2324 are input into the evaluation value calculator 2325 as information used for this calculation. Hereinafter, an example of calculating an evaluation value based on the area, an example of calculating an evaluation value based on the displacement, and an example of calculation that is a combination of both are described.

It should be noted that the present embodiment describes a configuration capable of executing both calculation methods of evaluation values; however, a configuration capable of any one of these may be employed.

(Calculation of Evaluation Values Based on Area)

As an example of calculating an evaluation value from the area of the image region calculated by the area calculator 2323, the evaluation value calculator 2325 may executes arithmetic processing of subtracting a product of the area of the image region and a preset weight from a preset maximum of evaluation values. This arithmetic processing may be expressed as the following equation, for example.

$$S_1 = S_{1,max} - a*(\text{Area}) \qquad [\text{Equation 1}]$$

Here, "$S_1$" indicates an evaluation value based on the area, "$S_{1,max}$" indicates a preset maximum of the concerned evaluation value, "a" indicates a preset weight, and "Area" indicates the area calculated by the area calculator 2323. The maximum $S_{1,max}$ and the weight a may be arbitrarily set. For example, the maximum $S_{1,max}$ is set to 100 and the weight a is set based on the magnitudes of this maximum and the area, and the like.

According to such arithmetic processing, the smaller the area is (that is, the smaller the error of the scanning position in the follow up imaging is), the greater the evaluation value $S_1$ becomes.

(Calculation of Evaluation Values Based on Displacement)

As an example of calculating an evaluation value from the displacement calculated by the displacement calculator 2324, the evaluation value calculator 2325 may executes arithmetic processing of subtracting a product of the displacement and a preset weight from a preset maximum of evaluation values. This arithmetic processing may be expressed as the following equation, for example.

$$S_2 = S_{2,max} - (b*DM + c*DS + d*DE) \qquad [\text{Equation 2}]$$

Here, "$S_2$" indicates an evaluation value based on the displacement, "$S_{2,max}$" indicates a preset maximum of the concerned evaluation value, "b", "c" and "d" indicate preset weights, and "DM", "DS" and "DE" indicate the displacements of middle points, scanning start points and scanning end points calculated by the displacement calculator 2324, respectively. The maximum $S_{2,max}$ and the weights b, c and d may be arbitrarily set. For example, the maximum $S_{2,max}$ is set to 100 and the weights b, c and d are set based on the magnitudes of this maximum and the displacement, and the like.

According to such arithmetic processing, the smaller the displacement is (that is, the smaller the error of the scanning position in the follow up imaging is), the greater the evaluation value $S_2$ becomes. It should be noted that the evaluation value is calculated by taking three types of points (middle points, scanning start points and scanning end points) into consideration in this example; however, the evaluation value may be calculated by taking one or two of these into consideration. Further, it is possible to calculate a displacement of points other than these and take it into consideration.

(Calculation of Evaluation Values Based on Area and Displacement)

As an example of calculating an evaluation value based on the area of the image region calculated by the area calculator 2323 and the displacement calculated by the displacement calculator 2324, the evaluation value calculator 2325 may utilize an arithmetic expression that is obtained by combining the respective cases described above. This arithmetic expression may be given by the following, for example.

$$S = S_{max} - a*(\text{Area}) - (b*DM + c*DS + d*DE) \qquad [\text{Equation 3}]$$

Here, "S" indicates an evaluation value based on the area and displacement, "$S_{max}$" indicates a preset maximum of the concerned evaluation value, "a" to "d" indicate preset weights, "Area" indicates the area calculated by the area calculator 2323, and "DM", "DS" and "DE" indicate the displacements of middle points, scanning start points and scanning end points calculated by the displacement calculator 2324, respectively. The maximum $S_{max}$ and the weights a to d may be arbitrarily set. For example, the maximum $S_{max}$ is set to 100 and the weights a to d are set based on the magnitudes of this maximum and the area, and the like.

According to such arithmetic processing, the smaller the area and/or the displacement are/is (that is, the smaller the error of the scanning position in the follow up imaging is), the greater the evaluation value S becomes.

Information of the evaluation value calculated by the evaluation value calculator 2325 is sent to the imaging-propriety judging part 233.

(Imaging-Propriety Judging Part)

The imaging-propriety judging part 233 judges propriety of follow up imaging based on the evaluation value calculated by the evaluation value calculator 2325. This processing may be carried out by comparing the evaluation value with a preset numerical value range.

Specific examples of processing executed by the imaging-propriety judging part 233 are described. In a case in which decrease of an error causes increase of evaluation value as described above, the imaging-propriety judging part 233 judges whether or not the calculated evaluation value is equal to or greater than a preset threshold. When the evaluation value is equal to or greater than the threshold, the imaging-propriety judging part 233 judges that the follow up imaging has been performed properly. Conversely, when the evaluation value is smaller than the threshold, the imaging-propriety judging part 233 judges that the follow up imaging has not been performed properly.

It should be noted that although only one threshold is used in the present example, two or more thresholds may be used to judge the propriety of follow up imaging in steps.

The imaging-propriety judging part 233 sends the judgment result to the controller 210. Further, any information used in the above processing executed by the image processor 230 and information intermediately generated in the above processing may be sent to the controller 210. Further, in a case in which the propriety of follow up imaging is presented by using the evaluation value itself, the imaging-propriety judging part 233 may not be provided.

The image processor 230 that functions as above comprises, for example, the aforementioned microprocessor, RAM, ROM, hard disk drive, circuit board, and so on. A computer program that causes the microprocessor to perform the above functions is stored in the storage device such as the hard disk drive in advance.

(User Interface)

A user interface 240 comprises the display 240A and the operation part 240B. The display 240A is configured to include a display device of the aforementioned arithmetic and control unit 200 and/or the display device 3. The operation part 240B is configured to include an operation device of the aforementioned arithmetic and control unit 200. The operation part 240B may also comprise various kinds of buttons, keys, etc. that are provided with the case of the ophthalmologic imaging apparatus 1 or outside thereof. For example, when the retinal camera unit 2 has a case that is similar to conventional retinal cameras, a joy stick, operation panel, etc. provided with the case may also be included in the operation part 240B. Furthermore, the display 240A may also include various display devices such as a touch panel etc. provided with the case of the retinal camera unit 2.

The display 240A and the operation part 240B do not need to be configured as separate components. For example, like a touch panel, it is possible to apply a device in which the display function and the operation function are integrated. In this case, the operation part 240B is configured to include the touch panel and a computer program. A content of operation to the operation part 240B is input into the controller 210 as an electrical signal. Further, operations and/or information input may be carried out by using a graphical user interface (GUI) displayed on the display 240A and the operation part 240B.

[Scanning with Signal Light and OCT Images]

Scanning modes of the signal light LS by the ophthalmologic imaging apparatus 1 may include, for example, horizontal scan, vertical scan, cross scan, radial scan, circular scan, concentric scan, helical scan, etc. These scanning modes are selectively used as necessary taking into account an observation site of a fundus, an analysis target (retinal thickness etc.), time required for scanning, the density of scanning, and so on.

The horizontal scan is one for scanning the signal light LS in the horizontal direction (x-direction). The horizontal scan includes a mode of scanning the signal light LS along multiple scanning lines extending in the horizontal direction arranged in the vertical direction (y-direction). In this mode, the interval of scanning lines may be arbitrarily set. Further, by setting the interval between adjacent scanning lines to be sufficiently narrow, it is possible to form the aforementioned three-dimensional image (three-dimensional scan). The vertical scan is performed in a similar manner.

The cross scan is one for scanning the signal light LS along a cross-shape trajectory consisting of two linear trajectories (line trajectories) orthogonal to each other. The radial scan is one for scanning the signal light LS along a radial trajectory consisting of multiple line trajectories arranged at predetermined angles. It should be noted that the cross scan is an example of the radial scan.

The circular scan is one for scanning the signal light LS along a circular trajectory. The concentric scan is one for scanning the signal light LS along multiple circular trajectories arranged concentrically around a predetermined center position. The circular scan is an example of the concentric scan. The helical scan is one for scanning the signal light LS along a helical trajectory while making the turning radius gradually smaller (or greater).

Since the galvano scanner 42 is configured to scan the signal light LS in the directions orthogonal to each other, the galvano scanner 42 is capable of scanning the signal light LS in the x-direction and the y-direction independently. Moreover, it is possible to scan the signal light LS along an arbitrary trajectory on the xy-plane by simultaneously controlling the directions of two galvano mirrors included in the galvano mirror 42. Thus, various kinds of scanning modes as described above may be realized.

By scanning the signal light LS in the modes described above, it is possible to obtain a cross sectional image in the plane spanned by the direction along the scanning line and the depth direction (z-direction) of the fundus. Moreover, in a case in which the interval between scanning lines is narrow, it is possible to obtain the aforementioned three-dimensional image.

(Display Control)

Examples of display control in the present embodiment are described. Display control is executed by the display controller 2111.

As a first display control, the display controller 2111 displays the reference front image and/or the follow-up front image on the display 240A and displays, over the front image(s), a reference scanning position image indicating the reference scanning position and a follow-up scanning position image indicating the follow-up scanning position based on the misregistration information obtained by the information obtaining part 231.

Here, instead of the misregistration information, the relative position information that is equivalent to it may be referred to. Further, the reference scanning position image is an example of a "first scanning position image" and the follow-up scanning position image is an example of a "second scanning position image".

When any one of the reference front image and the follow-up front image is to be displayed, the reference scanning position image and the follow-up scanning position image are displayed over this front image. On the other hand, when both of the reference front image and the follow-up front image are to be displayed, the reference scanning position image and the follow-up scanning position image are displayed over the respective front images or over only one front image.

The display controller 2111 may display the reference scanning position image and the follow-up scanning position image in different aspects from each other. For example, the two scanning position images may be displayed in different colors, different thicknesses, or different densities. Further, identification information (character string information, image information, etc.) may be attached to the respective scanning position images. Further, the two scanning position images may be displayed in different aspects all times, or the display aspects may be changed in response to a certain trigger.

Figure 8:
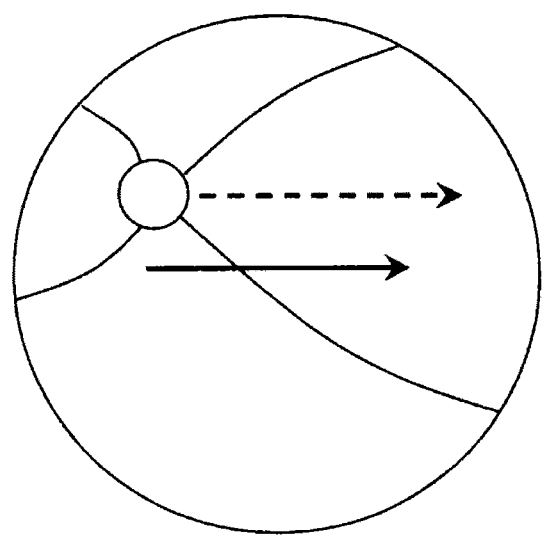
FIG. 8 is a schematic diagram for explaining an operation of an ophthalmologic imaging apparatus according to an embodiment.

FIG. 8 illustrates an example of information displayed by the first display control as described above. FIG. 8 illustrates a state in which the reference scanning position image (shown by a dotted line) and the follow-up scanning position image (shown by a solid line) are displayed over a follow-up front image expressing the morphology of the fundus. The follow-up scanning position image indicates the scanning position actually applied in the follow up imaging. Further, the reference scanning position image indicates an ideal scanning position with the assumption that the follow up imaging has been carried out with no errors. In the example shown in FIG. 8, the site indicated by the solid line has been scanned due to eye movement etc. although the site indicated by the dotted line should have been scanned.

As a second display control, the display controller 2111 displays information indicating the error in the scanning positions in the follow up imaging. For example, the display controller 2111 may display the evaluation value calculated by the evaluation value calculator 2325 on the display 240A. The evaluation value may be displayed individually, or displayed together with front image(s) and/or display information from the above first display control. Further, instead of the evaluation value or together with the evaluation value, the judgment result from the imaging-propriety judging part 233 may be displayed. This judgment result may be character string information such as "proper" or "improper", or image information.

[Actions and Effects]

Actions and effects of the ophthalmologic imaging apparatus 1 are explained.

The ophthalmologic imaging apparatus 1 is capable of carrying out follow up imaging. A photographing part (retinal camera unit 2) photographs the eye E and acquires a front image thereof. The cross sectional image forming part (optical system for OCT and image forming part 220) scans the eye E with light and forms a cross sectional image thereof. The storage 212 stores a first front image of the eye E and a second front image acquired in follow up imaging carried out with referring to the first front image. The information obtaining part (231) analyzes the first and second front images and obtains misregistration information between these front images. The calculator (232) calculates an evaluation value of an error in a scanning position in the follow up imaging based on the misregistration information. According to the ophthalmologic imaging apparatus 1, the degree of the error in the follow up imaging can be evaluated quantitatively.

Second Embodiment

Follow up imaging is carried out by referring to a reference front image acquired in the past. So, accuracy and precision of follow up imaging are influenced by the condition of the reference front image. In the present embodiment, an ophthalmologic imaging apparatus, in addition to arbitrary configuration described in the first embodiment, capable of judging propriety of a reference front image used in follow up imaging is described.

Figure 9:
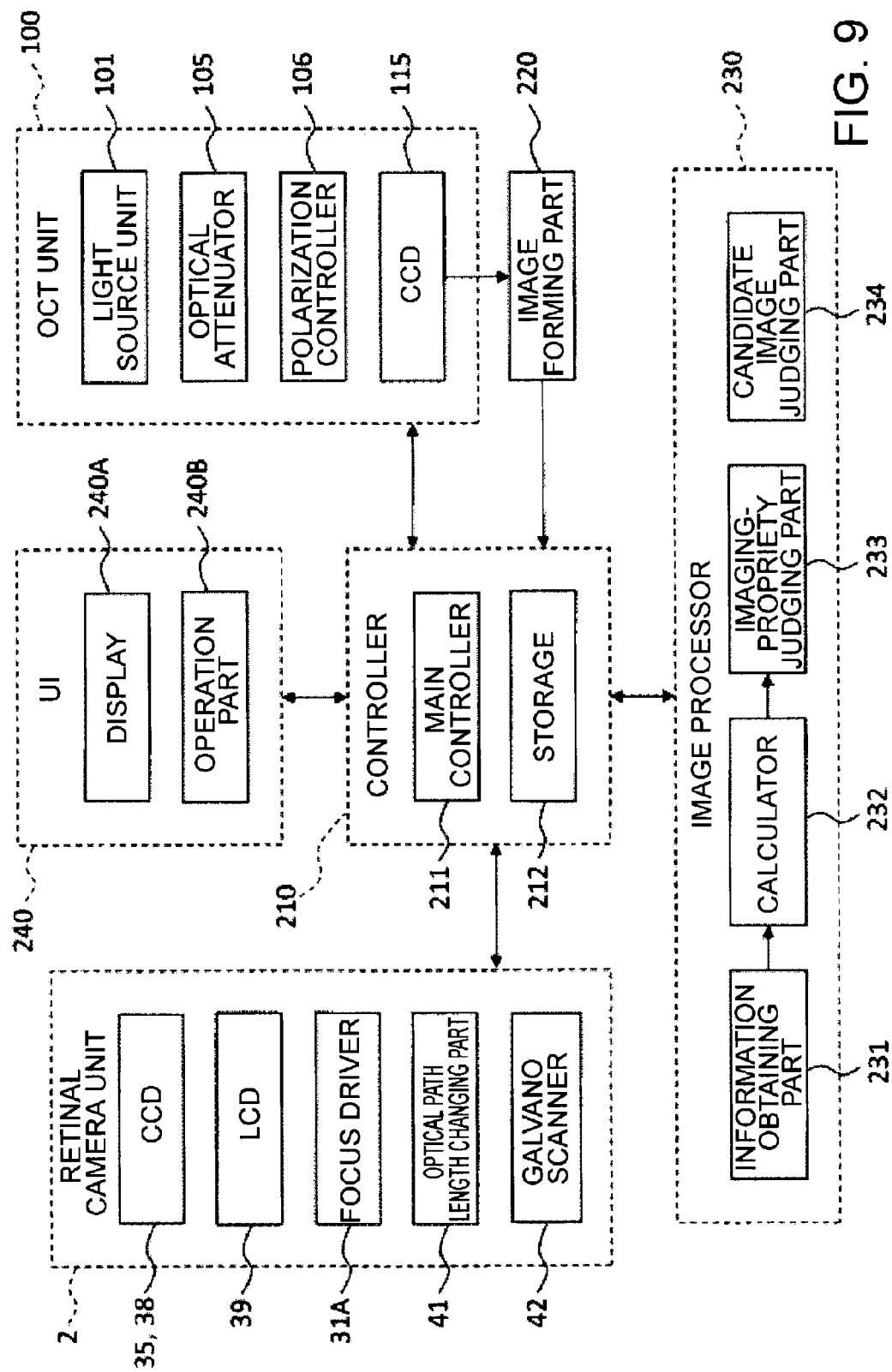
FIG. 9 is a schematic block diagram showing an example of a configuration of an ophthalmologic imaging apparatus according to an embodiment.

FIG. 9 illustrates a configuration example of the ophthalmologic imaging apparatus according to the present embodiment. The ophthalmologic imaging apparatus includes a candidate image judging part 234 in addition to the configuration of the first embodiment (see FIGS. 1 to 4). The candidate image judging part 234 is provided in the image processor 230. It should be noted that descriptions of configurations other than the candidate image judging part 234 are omitted unless otherwise stated since they are the same as the first embodiment.

When follow up imaging is carried out, the storage 212 stores one or more images (candidate images) to be a candidate for a reference front image. The candidate image judging part 234 analyzes the respective candidate images and judges whether or not the respective candidate images are suitable for the reference front image. It should be noted that when two or more candidate images are judged to be suitable, most suitable candidate image may be selected, for example.

Such judgment processing is carried out based on predetermined information relating to candidate images, for example. This information may be information relating to a real space or information relating to a frequency space. Examples of the information relating to the real space include flare amount and contrast. Examples of the relating to the frequency space include blur (dim) amount and frequency characteristic. Such information is obtained by the candidate image judging part 234.

Flare amount is a distribution of pixels of a candidate image having pixel values (luminance values etc.) greater than a preset threshold (maximum etc.), for example. This distribution may be a ratio of such pixels to whole pixels, for example. The candidate image judging part 234 judges that a candidate image is suitable for a reference front image when the flare amount obtained is equal to or less than a preset threshold, for example. Here, it is judged that the smaller the flare amount is, the more suitable for a reference image.

Contrast is obtained by arbitrary known technology executed based on pixel values (luminance values) of a candidate image, for example. The candidate image judging part 234 judges that a candidate image is suitable for a reference front image when the contrast obtained is equal to or greater than a preset threshold, for example. Here, it is judged that the greater the contrast is, the more suitable for a reference image.

Blur amount may be calculated based on signal intensities of spatial frequency components obtained by decomposing a candidate image into spatial frequencies. The candidate image judging part 234 judges that a candidate image is suitable for a reference front image when the blur amount obtained is equal to or less than a preset threshold, for example. Here, it is judged that the smaller the blur amount is, the more suitable for a reference image.

Frequency characteristic may be obtained by decomposing a candidate image into spatial frequencies and calculating a characteristic of the spatial frequency components obtained. The candidate image judging part 234 judges that a candidate image is suitable for a reference front image when the frequency characteristic obtained satisfies a preset condition, for example. Here, it is judged that the higher the degree of satisfaction of the condition is, the more suitable for a reference image.

The controller 210 executes informing control based on the judgment result from the candidate image judging part 234. The controller 210 and a part controlled in the informing control function as an example of an "informing part".

As a specific example of informing control, the display controller 2111 displays information indicating the judgment result on the display 240A. The displayed information may be character string information or image information indicating whether or not the candidate image is suitable for a reference image, for example. Further, it is possible to display one or more candidate images (or their thumb nails) processed in the judgment by the candidate image judging part 234, and also display a list of information indicating the judgment results. Further, it is possible to display a list of imaging information of candidate images in the imaging information display of the patient selecting screen described in the first embodiment, and also display the judgment results in this list. In a case of carrying out such informing control, the display controller 2111 functions as an example of an "informing controller".

Informing control is not limited to such display control. For example, it may be configured that the controller 210 controls an audio output part (not illustrated) to output audio information indicating the judgment result.

it is possible to prohibit follow up imaging based on a candidate image when the judgment result that this candidate image is unsuitable for a reference front image is obtained. As a specific example thereof, the controller 210 may prohibit optical scanning by the cross sectional image forming part in response to acquisition of the judgment result that the candidate image is not suitable for a reference front image. The prohibition here means a control mode in which OCT measurement is not carried out even when an instruction for starting OCT measurement is input. The controller 210 that performs such control is an example of a "prohibition controller". Further, supposing cases in which follow up imaging is carried out by referring to a candidate image that has been judged as "unsuitable", for example, a configuration may be employed in which an operation for canceling such prohibition can be done.

According to such an ophthalmologic imaging apparatus, it is possible to judge whether a reference image used in follow up imaging is suitable, thereby carrying out follow up imaging with referring to a preferable reference front image. Therefore, the degree of an error in follow up imaging is evaluated quantitatively as in the first embodiment, and also precision and accuracy of follow up imaging may be improved.

Figure 10:
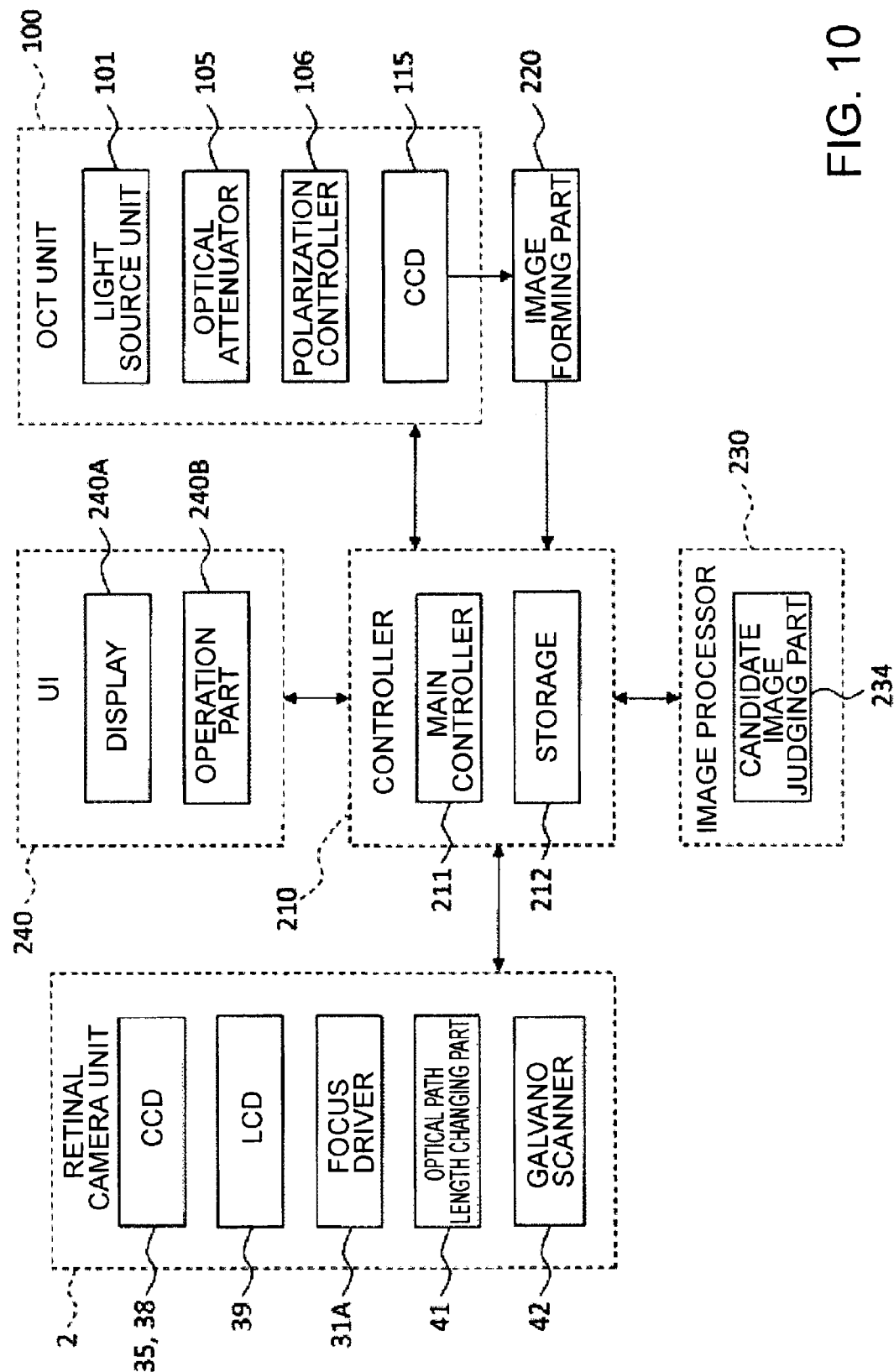
FIG. 10 is a schematic block diagram showing an example of a configuration of an ophthalmologic imaging apparatus according to an embodiment.

An ophthalmologic imaging apparatus may be configured to include features of the second embodiment and not include features of the first embodiment. Such an ophthalmologic imaging apparatus may have a configuration illustrated in FIG. 10, for example.

Specifically, this ophthalmologic imaging apparatus is capable of carrying out follow up imaging and includes a photographing part, a cross sectional image forming part, a storage, a candidate image judging part and an informing part. The photographing part (retinal camera unit 2) photographs the eye and acquires a front image thereof. The cross sectional image forming part (optical system for OCT measurement and the image forming part 220) scans the eye with light and forms a cross sectional image thereof. The storage (storage 212) stores one or more candidate images for a front image referred to in follow up imaging. The candidate image judging part (candidate image judging part 234) analyzes the candidate images and judges whether or not the candidate images are suitable for a reference front image. The informing part performs informing based on the judgment result from the candidate image judging part.

According to such an ophthalmologic imaging apparatus, it is possible to judge whether a reference image used in follow up imaging is suitable, thereby carrying out follow up imaging with referring to a preferable reference front image. Therefore, accuracy of follow up imaging may be improved. It should be noted that processing executed by the candidate image judging part 234 may be the same as above. Further, it may be configured to carry out display control and informing control described above.

Third Embodiment

The present embodiment describes an ophthalmologic image processing apparatus that receives information from an ophthalmologic imaging apparatus capable of carrying out follow up imaging and processes the received information. The ophthalmologic image processing apparatus is configured to include a computer, for example. Further, part of the ophthalmologic image processing apparatus may be arranged outside a computer. For example, storage may be a database on a network.

Figure 11:
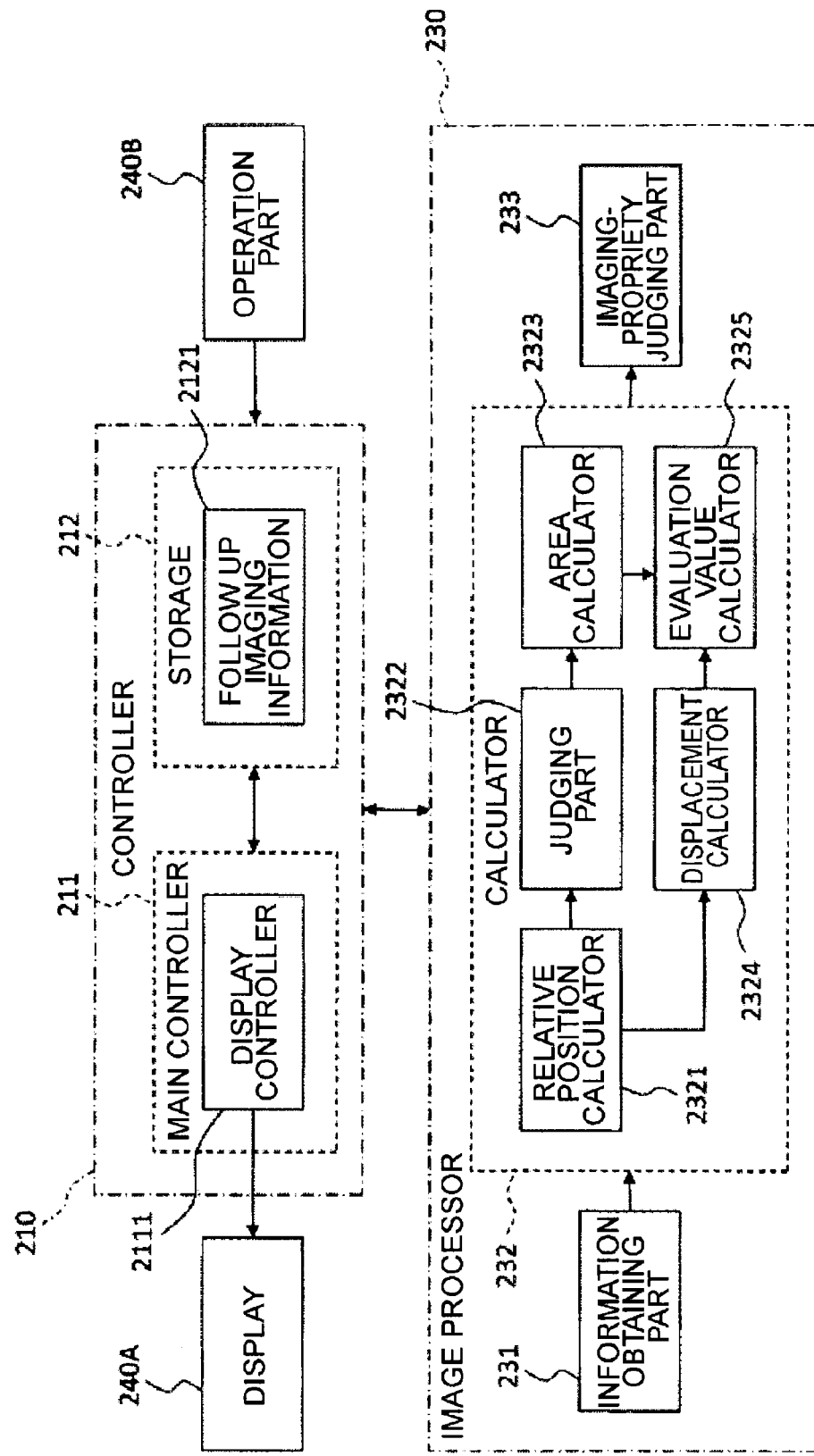
FIG. 11 is a schematic block diagram showing an example of a configuration of an ophthalmologic image processing apparatus according to an embodiment.

FIG. 11 illustrates a configuration example of an ophthalmologic image processing apparatus of the present embodiment. This ophthalmologic image processing apparatus includes a configuration similar to the first embodiment (see FIG. 4). On the other hand, this ophthalmologic image processing apparatus does not include the photographing part (retinal camera unit 2) and the cross sectional image forming part (optical system for OCT measurement and the image forming part 220). Further, the ophthalmologic image processing apparatus does not include computer programs for controlling these excluded components. Hereinafter, descriptions of components similar to the first embodiment are omitted unless otherwise stated.

The ophthalmologic image processing apparatus of the present embodiment processes images acquired by follow up imaging and include at least a storage, an information obtaining part and a calculator. The storage (storage 212) stores a first front image of an eye and a second front image acquired in follow up imaging carried out with referring to the first front image. The information obtaining part (information obtaining part 231) analyzes the first and second front images and obtains misregistration information between these front images. The calculator (calculator 232) calculates an evaluation value of an error in a scanning position of light in the follow up imaging based on the misregistration information. Configurations and operations of other components correspond to the first embodiment.

According to such an ophthalmologic image processing apparatus, the degree of the error in the follow up imaging carried out by an ophthalmologic imaging apparatus can be evaluated quantitatively.

Modification Examples

The configuration described above is merely illustrations for favorably implementing the present invention. Therefore, it is possible to make arbitrary modification (omission, replacement, addition, etc.) within the scope of the present invention.

In the first and second embodiments, the optical path length difference between the optical path of the signal light LS and the optical path of the reference light LR is changed by varying the position of the optical path length changing part 41; however, a method for changing the optical path length difference is not limited to this. For example, it is possible to change the optical path length difference by providing a reference mirror (reference mirror) in the optical path of the reference light and moving the reference mirror in the advancing direction of the reference light to change the optical path length of the reference light. Further, the optical path length difference may be changed by moving the retinal camera unit 2 and/or the OCT unit 100 with respect to the eye E to change the optical path length of the signal light LS. Moreover, in a case that an object is not a living site or the like, it is also effective to change the optical path length difference by moving the object in the depth direction (z-direction).

Computer programs for implementing the above embodiments can be stored in any kind of recording medium that can be read by a computer. As such recording media, for example, an optical disk, a semiconductor memory, a magneto-optic disk (CD-ROM, DVD-RAM, DVD-ROM, MO, and so on), and a magnetic storage (a hard disk, a floppy Disk™, ZIP, and so on) can be used.

In addition, it is possible to transmit/receive this program through a network such as internet or LAN etc.

EXPLANATION OF SYMBOLS 1 ophthalmologic imaging apparatus
2 retinal camera unit
10 illumination optical system
30 imaging optical system
31 focusing lens
31A focus driver
41 optical path length changing part
42 galvano scanner
50 alignment optical system
60 focus optical system
100 OCT unit
101 light source unit
105 optical attenuator
106 polarization controller
115 CCD image sensor
200 arithmetic and control unit
210 controller
211 main controller
2111 display controller
212 storage
2121 follow up imaging information
220 image forming part
230 image processor
231 information obtaining part
232 calculator
2321 relative position calculator
2322 judging part
2323 area calculator
2324 displacement calculator
2325 evaluation value calculator
233 imaging-propriety judging part
234 candidate image judging part
240A display
240B operation part
E eye
Ef (eye) fundus
LS signal light
LR reference light
LC interference light

What is claimed is:

1. An ophthalmologic imaging apparatus capable of carrying out follow up imaging for acquiring a cross sectional image by referring to a front image of an eye acquired in the past and scanning the same position as before with light, comprising:
    a photographing part configured to photograph the eye and acquire a front image thereof;
    a cross sectional image forming part configured to scan the eye with light and form a cross sectional image thereof;
    a storage configured to store a first front image of the eye and a second front image acquired in follow up imaging carried out with referring to the first front image;
    an information obtaining part configured to analyze the first and second front images and obtain misregistration information between these front images; and
    a calculator configured to calculate an evaluation value of an error in a scanning position in the follow up imaging based on the misregistration information.

2. The ophthalmologic imaging apparatus of claim 1, wherein
    the storage further stores a first scanning position that is a scanning position, in the first front image, of a cross sectional image formed associated with the first front image and a second scanning position that is a scanning position, in the second front image, of a cross sectional image formed associated with the second front image,
    the calculator comprises an area calculator configured to calculate an area of an image region defined by the first and second scanning positions based on the misregistration information, and
    the calculator calculates the evaluation value based on the area of the image region.

3. The ophthalmologic imaging apparatus of claim 2, wherein
    the calculator comprises a judging part configured to judge, based on the misregistration information, whether or not the first and second scanning positions have a common position, and the area calculator calculates the area by executing different arithmetic processing according to the judgment result from the judging part.

4. The ophthalmologic imaging apparatus of claim 3, wherein
each of the first and second scanning positions is of a line-segment shape,
the common position is an intersection point of these scanning positions of the line-segment shape,
when it is judged that the intersection point exists, the area calculator calculates a sum of an area of a first triangle formed by the intersection point and end points of the first and second scanning positions located on one side from the intersection point and an area of a second triangle formed by the intersection point and end points of the first and second scanning positions located on the other side, and sets the calculation result of this sum as the area of the image region.

5. The ophthalmologic imaging apparatus of claim 4, wherein when the intersection point is located at an endpoint of the first scanning position and/or an endpoint of the second scanning position, the area calculator obtains the area of the first triangle by calculating an area of a triangle formed by the intersection point and endpoints of the first and second scanning positions located on the opposite side to the intersection point, and sets the calculation result of this area as the area of the image region.

6. The ophthalmologic imaging apparatus of claim 3, wherein
each of the first and second scanning positions is of a line-segment shape,
the common position is an intersection point of these scanning positions of the line-segment shape,
when it is judged that the intersection point does not exist, the area calculator calculates an area of a quadrangle having the first and second scanning positions as two sides and line segments connecting endpoints of the first scanning position and endpoints of the second scanning position as other two sides, and sets the calculation result of this area as the area of the image region.

7. The ophthalmologic imaging apparatus of claim 2, wherein in the processing for calculating the evaluation value from the area of the image region, the calculator executes arithmetic processing of subtracting a product of the area of the image region and a preset weight from a preset maximum of evaluation values.

8. The ophthalmologic imaging apparatus of claim 2, comprising a first display controller configured to display the first and/or second front images on a display and displays a first scanning position image indicating the first scanning position and a second scanning position image indicating the second scanning position over the front images based on the misregistration information.

9. The ophthalmologic imaging apparatus of claim 8, wherein the first display controller displays the first and second scanning position images in different aspects from each other.

10. The ophthalmologic imaging apparatus of claim 1, wherein
the storage further stores a first scanning position that is a scanning position, in the first front image, of a cross sectional image formed associated with the first front image and a second scanning position that is a scanning position, in the second front image, of a cross sectional image formed associated with the second front image,
the calculator comprises a displacement calculator configured to calculate a displacement between the first and second scanning positions based on the misregistration information, and
the calculator calculates the evaluation value based on the displacement.

11. The ophthalmologic imaging apparatus of claim 10, wherein the displacement calculator calculates a displacement between a preset position in the first scanning position and a position in the second scanning position corresponding to this preset position.

12. The ophthalmologic imaging apparatus of claim 11, wherein
each of the first and second scanning positions is of a line-segment shape,
the preset position includes at least one of a start point, end point and middle point of scanning in the scanning positions of the line-segment shape.

13. The ophthalmologic imaging apparatus of claim 10, wherein in the processing for calculating the evaluation value from the displacement, the calculator executes arithmetic processing of subtracting a product of the displacement and a preset weight from a preset maximum of evaluation values.

14. The ophthalmologic imaging apparatus of claim 1, wherein
the storage further stores a first scanning position that is a scanning position, in the first front image, of a cross sectional image formed associated with the first front image and a second scanning position that is a scanning position, in the second front image, of a cross sectional image formed associated with the second front image,
the calculator comprises:
an area calculator configured to calculate an area of an image region defined by the first and second scanning positions based on the misregistration information; and
a displacement calculator configured to calculate a displacement between the first and second scanning positions based on the misregistration information, and
the calculator calculates the evaluation value based on the area of the image region and the displacement.

15. The ophthalmologic imaging apparatus of claim 1, comprising a second display controller configured to display the evaluation value calculated by the calculator on a display.

16. The ophthalmologic imaging apparatus of claim 1, comprising an imaging-propriety judging part configured to judge propriety of follow up imaging based on the evaluation value calculated by the calculator.

17. The ophthalmologic imaging apparatus of claim 1, wherein the information obtaining part calculates a parallel shift error and rotational shift error between the first and second front images as the misregistration information.

18. The ophthalmologic imaging apparatus of claim 1, wherein the storage stores, as the second front image, front images acquired first and last in the period in which light scanning is carried out in follow up imaging.

19. The ophthalmologic imaging apparatus of claim 1, wherein
when follow up imaging is carried out, the storage stores one or more candidate images for the first front image, and
the ophthalmologic imaging apparatus comprises:
a candidate image judging part configured to analyze the candidate images and judge whether or not the candidate images are suitable for the first front image; and an informing part configured to performs informing based on the judgment result from the candidate image judging part.

20. The ophthalmologic imaging apparatus of claim 19, wherein the candidate image judging part executes judgment based on pixel values of the candidate images.

21. The ophthalmologic imaging apparatus of claim 19, wherein the candidate image judging part calculates spatial frequency components of the candidate images and executes judgment based on the spatial frequency components.

22. The ophthalmologic imaging apparatus of claim 19, wherein the informing part comprises an informing controller configured to display information indicating the judgment result on a display.

23. The ophthalmologic imaging apparatus of claim 19, comprising a prohibition controller configured to prohibit light scanning by the cross sectional image forming part in response to acquisition of the judgment result that the candidate images are not suitable for the front image referred to.

24. An ophthalmologic imaging apparatus capable of carrying out follow up imaging for acquiring a cross sectional image by referring to a front image of an eye acquired in the past and scanning the same position as before with light, comprising:
   a photographing part configured to photograph the eye and acquire a front image thereof;
   a cross sectional image forming part configured to scan the eye with light and form a cross sectional image thereof;
   a storage configured to store one or more candidate images for a front image referred to in follow up imaging;
   a candidate image judging part configured to analyze the candidate images and judge whether or not the candidate images are suitable for the front image referred to; and
   an informing part configured to performs informing based on the judgment result from the candidate image judging part.

25. An ophthalmologic image processing apparatus that processes images acquired by follow up imaging for acquiring a cross sectional image by referring to a front image of an eye acquired in the past and scanning the same position as before with light, comprising:
   a storage configured to store a first front image of the eye and a second front image acquired in follow up imaging carried out with referring to the first front image;
   an information obtaining part configured to analyze the first and second front images and obtain misregistration information between these front images; and
   a calculator configured to calculate an evaluation value of an error in a scanning position of the light in the follow up imaging based on the misregistration information.

* * * * *